United States Patent
Ruchet et al.

(10) Patent No.: US 9,733,616 B2
(45) Date of Patent: Aug. 15, 2017

(54) PORTABLE DIGITAL HOLOGRAPHIC PROBE FOR THE INSPECTION OF OPTICAL FIBER CONNECTORS, AND INSPECTION SYSTEM AND METHOD FOR THE SAME

(71) Applicant: EXFO INC., Québec (CA)

(72) Inventors: Bernard Ruchet, Québec (CA); Normand Cyr, Québec (CA)

(73) Assignee: EXFO INC., Quebec (CA)

( * ) Notice: Subject to any disclaimer, the term of this patent is extended or adjusted under 35 U.S.C. 154(b) by 398 days.

(21) Appl. No.: 14/368,625

(22) PCT Filed: Dec. 21, 2012

(86) PCT No.: PCT/CA2012/050936
§ 371 (c)(1),
(2) Date: Jun. 25, 2014

(87) PCT Pub. No.: WO2013/097041
PCT Pub. Date: Jul. 4, 2013

(65) Prior Publication Data
US 2014/0327735 A1    Nov. 6, 2014

Related U.S. Application Data

(60) Provisional application No. 61/580,844, filed on Dec. 28, 2011.

(51) Int. Cl.
*G01B 9/021* (2006.01)
*G03H 1/08* (2006.01)
(Continued)

(52) U.S. Cl.
CPC .......... *G03H 1/0866* (2013.01); *G01B 9/021* (2013.01); *G01M 11/088* (2013.01); *G01N 21/94* (2013.01);
(Continued)

(58) Field of Classification Search
CPC ... G03H 1/0866; G01M 11/088; G02B 6/385; G01B 9/021; G01B 9/023
See application file for complete search history.

(56) References Cited

U.S. PATENT DOCUMENTS 4,589,723 A    5/1986  Doi et al.
4,696,572 A    9/1987  Ono
(Continued)

FOREIGN PATENT DOCUMENTS

CN    201589600 U    *  9/2010
JP    61048818 A       3/1986
(Continued)

OTHER PUBLICATIONS

Abdelsalam et al., Real-time dual-wavelength digital holographic microscopy based on polarizing separation, Optics Communications, Elsevier, p. 233-237, Oct. 5, 2011.
(Continued)

*Primary Examiner* — Michael A Lyons
(74) *Attorney, Agent, or Firm* — Erise IP, P.A.

(57) ABSTRACT

A portable inspection probe for the inspection of a recessed mating surface of an optical fiber connector is provided. In one variant, the portable inspection probe includes a digital holographic detection module operable to digitally record a hologram of the recessed mating surface, and a rigid probe tip configured to be optically coupled to the digital holographic detection module and shaped to provide optical access to the recessed mating surface. In another variant, the portable inspection probe is to be used with a rigid probe tip connectable thereto, and the digital holographic detection module includes a probing optical assembly not traversed by a reference beam and configured to direct an object beam onto the recessed mating surface and to collect the object beam upon reflection thereof by the recessed mating surface.

(Continued)

An inspection system and an inspection method are also provided.

23 Claims, 12 Drawing Sheets

(51) Int. Cl.
    *G02B 6/38*     (2006.01)
    *G02B 21/00*     (2006.01)
    *G01N 21/94*     (2006.01)
    *G01M 11/08*     (2006.01)

(52) U.S. Cl.
    CPC .......... *G02B 6/385* (2013.01); *G02B 21/0016* (2013.01); *G01N 2201/0627* (2013.01)

(56) References Cited

U.S. PATENT DOCUMENTS

| | | | |
|---|---|---|---|
| 5,459,564 A | 10/1995 | Chivers | |
| 6,078,392 A | 6/2000 | Thomas et al. | |
| 6,525,821 B1 | 2/2003 | Thomas et al. | |
| 6,747,771 B2 | 6/2004 | Thomas et al. | |
| 6,751,017 B2 | 6/2004 | Cassady | |
| 7,002,691 B2 | 2/2006 | Thomas et al. | |
| 7,068,375 B2 | 6/2006 | Voelkl | |
| 7,127,109 B1 * | 10/2006 | Kim | G03H 1/0005 356/512 |
| 7,148,969 B2 | 12/2006 | Thomas et al. | |
| 7,264,479 B1 | 9/2007 | Lee | |
| 7,327,464 B2 | 2/2008 | Hwang et al. | |
| 7,336,884 B2 | 2/2008 | Zhou et al. | |
| 7,724,413 B2 | 5/2010 | Koyata et al. | |
| 7,880,891 B1 | 2/2011 | Kim | |
| 7,924,430 B2 | 4/2011 | Georges, III | |
| 7,924,434 B2 | 4/2011 | Hwang et al. | |
| 8,040,521 B2 | 10/2011 | Pfaff | |
| 2009/0146412 A1 | 6/2009 | Schoenoff et al. | |
| 2009/0244667 A1 | 10/2009 | Frentz et al. | |
| 2010/0253986 A1 * | 10/2010 | Awatsuji | G03H 1/0443 359/10 |

FOREIGN PATENT DOCUMENTS

| | | | |
|---|---|---|---|
| WO | WO 2004094942 A2 * | 11/2004 | ........... G03H 1/0406 |
| WO | 2009148407 A1 | 12/2009 | |

OTHER PUBLICATIONS

Bjelkhagen, H.I., What is possible with holographic endoscopy?, SPIE Digital Library, vol. 1647, p. 66-74, 1992.

Thomas et al., Direct to digital holography for semiconductor wafer defect detection and review, Proceedings of SPIE, vol. 4692, p. 180-194, 2002.

Baumbach et al., Improvement of accuracy in digital holography by use of multiple holograms, Applied Optics, Optical Society of America, vol. 45 No. 24, p. 6077-6085, Aug. 20, 2006.

Kim, M.K., Principles and techniques of digital holographic microscopy, SPIE Reviews, vol. 1, p. 018005-1-18005-50, May 14, 2010.

Kubota et al., Very efficient speckle contrast reduction realized by moving diffuser device, Applied Optics, Optical Society of America, vol. 49, No. 23, p. 4385-4391, Aug. 10, 2010.

Kuratomi et al., Speckle reduction mechanism in laser rear projection displays using a small moving diffuser, J. Opt. Soc. Am., vol. 27, No. 8, p. 1812-1817, 2010.

Riechert et al., Low-speckle laser projection with a broad-area vertical-cavity surface-emitting laser in the nonmodal emission regime, Applied Optics, Optical Society of America, vol. 48, No. 4, p. 792-798, Feb. 1, 2009.

Schmitt, J.M., Array detection for speckle reduction in optical coherence microscopy, Phys. Med. Biol. 42, p. 1427-1439, IOP Publishing Ltd, 1997.

Yonemura et al., Endoscopic hologram interferometry using fiber optics, Applied Optics, vol. 20, No. 9, p. 1664-1667, May 1, 1981.

Von Bally et al., Holographic endoscopy with gradiant-index optical imaging systems and optical fibers, Applied Optics, vol. 25, No. 19, p. 3425-3429, Oct. 1, 1986.

Von Bally et al., Gradiant-index optical systems in holographic endoscopy, Applied Optics, vol. 23, No. 11, p. 1725-1729, Jun. 1, 1984.

Colomb et al., Digital holographic reflectometry, Optics Express, vol. 18, No. 4, p. 3719-3731, Feb. 15, 2010.

Price et al., Improving resolution in microscopic holography by computationally fusing multiple, obliquely illuminated object waves in the Fourier domain, Applied Optics, vol. 46, No. 6, p. 827-833, Feb. 20, 2007.

Kim, M.K., Special techniques of digital holography, Digital Holographic Microscopy: Principles, Techniques and Applications, Chapter 10, Springer Series in Optical Sciences 162, p. 129-147, 2011.

Thomas et al., Direct to digital holography for high aspect ratio inspection of semiconductor wafers; Date Published Online: Sep. 30, 2003; AIP Publishing; Austin, Texas (USA).

\* cited by examiner

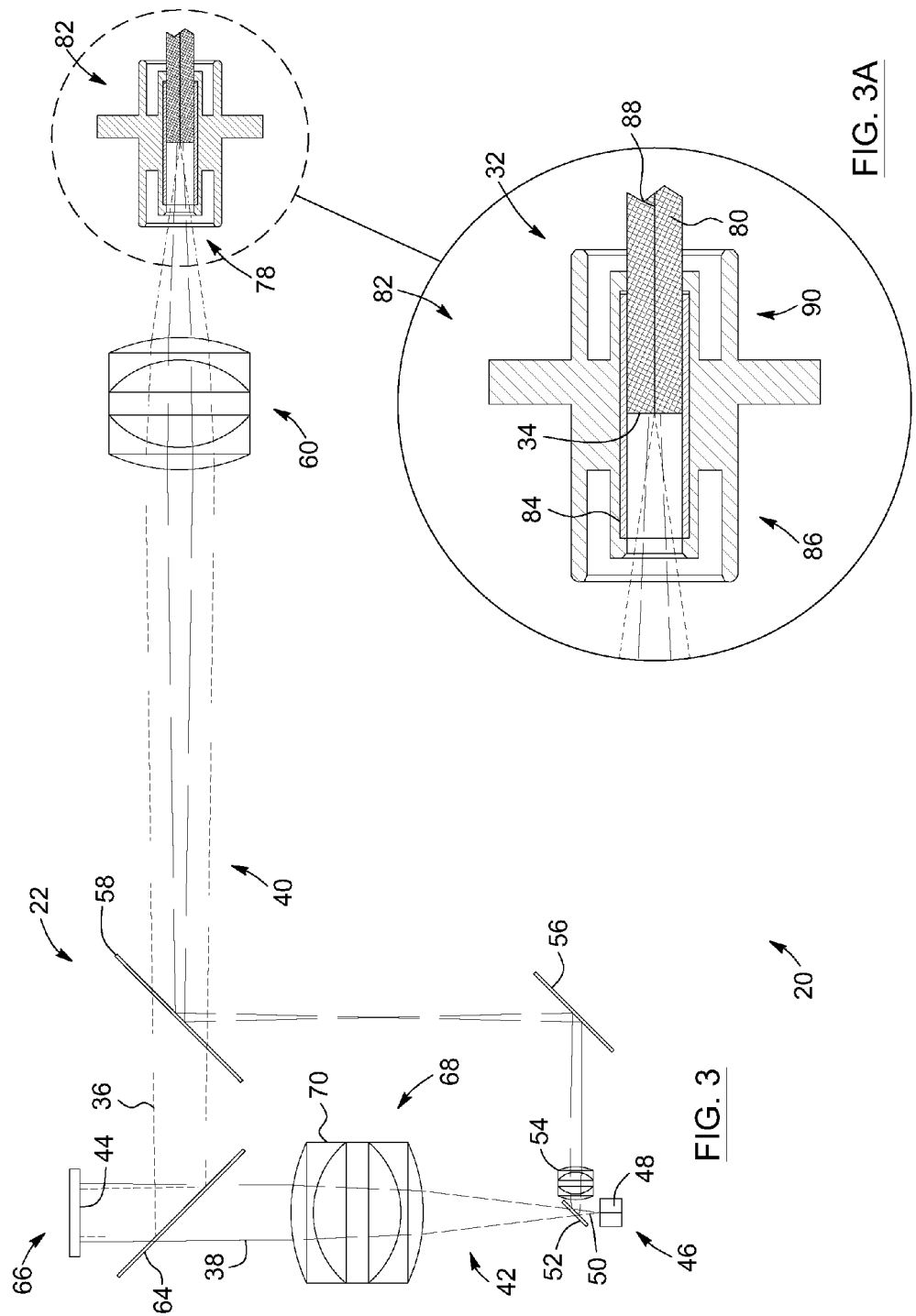

ET US 9,733,616 B2

PORTABLE DIGITAL HOLOGRAPHIC PROBE FOR THE INSPECTION OF OPTICAL FIBER CONNECTORS, AND INSPECTION SYSTEM AND METHOD FOR THE SAME

RELATED APPLICATIONS

The present application is a national stage application under 35 U.S.C. §371 of International Application No. PCT/CA2012/050936, filed 21 Dec. 2012, and which claims priority from U.S. Provisional Application No. 61/580,844, filed 28 Dec. 2011. The above-referenced applications are hereby incorporated by reference into the present application in their entirety.

FIELD OF THE INVENTION

The present specification relates to the field of optical fiber inspection, and more particularly concerns a portable inspection probe using digital holography that is suitable for detecting defects and foreign particles on the mating surface of an optical fiber connector, and an inspection system and a method for the same.

BACKGROUND

Optical fiber networks lie at the core of modern telecommunication systems and infrastructures. Employing optical fibers for transmitting information requires particular care to ensure efficient propagation and reception of optical signals. In this regard, the quality and cleanliness of optical fiber connectors represent important factors for achieving adequate system performances. Optical fiber connectors are key optical components that interconnect the network elements by allowing light to travel between two fibers or between one fiber and another optical component with minimal losses and without requiring splicing. Any contamination or damage on the mating surface of an optical fiber connector may severely degrade signal integrity. Since connectors are susceptible to defects that are not immediately discernible by the naked eye, the development of reliable and accurate inspection tools constitutes an important technological challenge.

Poor quality mating of optical fiber connectors arises most frequently when, for at least one of the connectors, contaminants or defects are present on the endface of the ferrule or, yet more deleteriously, on the endface of the optical fiber enclosed therein. The ferrule and enclosed optical fiber correspond to the end portion of a connector. The ferrule protrudes from the connector body in order to be inserted into a coupling device, such as a bulkhead adapter. The ferrule is generally a long, thin cylindrical structure, typically made of glass, metal, ceramic or plastic, that is concentrically bored along its longitudinal axis. This longitudinal bore defines a space for receiving the end of an optical fiber. The ferrule supports the end of the optical fiber and acts as a fiber alignment mechanism when interconnecting the fiber to another fiber, a transmitter or a receiver. By way of example, FIGS. 1A and 1B (PRIOR ART) show a schematic representation of an optical fiber 88 mounted into the ferrule 80 of an optical fiber connector 32 (FIG. 1A) and of a typical bulkhead adapter 82 defining a connector alignment sleeve 84 for mating the optical fiber 88 to another optical device (FIG. 1B).

Upon insertion of the optical fiber inside the ferrule, the end portion of the optical fiber extends slightly beyond the endface of the ferrule. This excess length may then be trimmed off for termination and polished so that the resulting endface of the optical fiber is substantially flush with the endface of the ferrule. The endface of the ferrule is also typically polished, generally to a spherically-shaped surface having a radius of curvature between about 7 mm and 25 mm for ultra physical contact (UPC) connectors. Alternatively, ferrules of some connector types may be polished at a radius of curvature between about 5 mm and 12 mm and at a mean angle having a normal at 7 or 8 degrees with respect to the longitudinal bore of the ferrule into which the end part of the fiber has been inserted. Such connectors, commonly denoted as angled physical contact (APC) connectors, may significantly reduce the degree of back-reflection or optical return loss (ORL) of an unmated connector with respect to the −14-dB ORL of an unmated connector for which the ferrule has not been polished to such an angle. In addition, when connected together inside a coupling device such as an adapter, mated APC connectors generally exhibit a lower residual ORL than their non-angled counterparts.

It will be understood herein that throughout this specification, the expression "endface of the ferrule" is intended to refer to the common end surface of both the ferrule and the fiber. It will also be understood that maintaining good conditions at the endface of the ferrule is important for minimizing optical losses and the generation of excessive ORL at the interface between two optical fibers.

Several inspection techniques and devices, suitable for field use in deployed optical network, have been devised to evaluate polish quality and cleanliness of connectors and other fiber terminations, most notably fiber-optic microscopes and portable video fiber inspection probes.

Fiber-optic microscopes having an adapter to hold the connector in position and a light source for proper illumination can be used as inspection tools for optical fiber connectors. Various fiber-optic microscopes have been developed for such applications, ranging from simple and inexpensive designs to systems having more sophisticated capabilities and options. However, since the ferrule (male) of the optical fiber connector to be inspected is inserted at one end of the instrument and the user must look in at the other end, fiber-optic microscopes are not designed for inspecting (female) connector bulkhead adapters located in patch panels.

Portable video fiber inspection probes constitute another option for evaluating optical fiber connectors. Unlike fiber-optic microscopes, video fiber inspection probes facilitate the inspection of hard-to-reach connectors located on patch panels and bulkhead adapters. These portable probes are equipped with a light-emitting diode (LED) light source for illuminating the connector, a recording element, including for example a charge-coupled device (CCD) or complementary metal-oxide-semiconductor (CMOS) array, for capturing digital images, as well as adapter tips for most connectors available on the market. Image display can be realized by connecting the probe to an external video screen, a personal computer, or a handheld monitor for fast and efficient inspection.

The above-mentioned prior art is based upon detection of only the spatially-resolved optical power of the imaged ferrule endface, which is directly proportional to the square of the optical electric field amplitude. Such approaches may be termed "direct detection" methods, since they are only sensitive to the optical power, that is, they are not sensitive to the phase of the optical electrical field.

More detailed information leading to improved ferrule endface inspection and characterization may be gleaned by measuring both the phase and amplitude of the light providing the image. An example of such an approach employs "white light" Michelson interferometry, generally in tandem with a "direct-detection" microscope, and the resulting images are displayed on a video screen. Such an approach may be denoted as an interferometric approach, for which the interference occurs between two recombined light beams, originating from a common source, where one of the beams has reflected from the mating surface under inspection and the other beam has reflected from a reference surface. An example of such a method is taught in U.S. Pat. No. 5,459,564 to Chivers, and embodied in the ZX-1 mini-PMS+ product (trade name) commercialized by DORC® Instruments, Inc. The interference fringes produced by such a Michelson interferometer may provide information related to the geometry of the polished surface (e.g. radius of curvature, apex offset, and the like) as well as to the identification of surface defects. However, the design is inherently bulky and unwieldy, thus rendering such an instrument impractical for portable testing in an optical network.

Inspection probes currently deployed for use in the field have the drawback that the accuracy and reliability of the measurements made with them depend essentially on the operator's ability to correctly focus the instrument. When proper focus is not achieved, the analysis software inside the instrument or provided in an external processing unit may not be able to compensate for operator mistakes in adjusting the focus of the device.

Moreover, when multi-fiber connectors, such as MTP, MT-RJ, and MPO types, need to be inspected with a "direct-detection" microscope, each fiber comprising the multi-fiber connector needs to be disposed in the focal plane and within the numerical aperture of the microscope objective by suitable mechanical displacement means. Examples of such mechanical displacement means are taught in U.S. Pat. No. 6,751,017 to Cassady and U.S. Pat. No. 7,336,884 to Zhou et al. A drawback of such approaches is that they involve time-consuming manual adjustment by the user, and a separate image usually must be acquired for each fiber in the multi-fiber connector.

In light of the above, there therefore exists a need in the art for an improved portable inspection probe suitable for the inspection of mating surfaces of optical fiber connectors, which provides fast and reliable performance and that alleviates at least some of the above-mentioned drawbacks.

SUMMARY

According to an aspect of the invention, there is provided a portable inspection probe for the inspection of a recessed mating surface of an optical fiber connector, the portable inspection probe comprising:
  a digital holographic detection module operable to digitally record a hologram of the recessed mating surface; and
  a rigid probe tip configured to be optically coupled to the digital holographic detection module and shaped to provide optical access to the recessed mating surface.

According to another aspect of the invention, there is provided a portable inspection probe for the inspection of a recessed mating surface of an optical fiber connector to be used with a rigid probe tip connectable thereto and shaped to provide optical access to the recessed mating surface, the portable inspection probe comprising a digital holographic detection module operable to digitally record a hologram of the recessed mating surface.

According to another aspect of the invention, there is provided a portable inspection probe for the inspection of a recessed mating surface of an optical fiber connector to be used with a rigid probe tip connectable thereto and shaped to provide optical access to the recessed mating surface, the portable inspection probe comprising:
  a digital holographic detection module operable to digitally record a hologram of the recessed mating surface, the digital holographic detection module being configured to propagate an object beam and a reference beam along respective object and reference optical paths, the digital holographic detection module comprising a probing optical assembly not traversed by the reference beam and configured to direct the object beam onto the recessed mating surface and to collect the same upon reflection thereof by the recessed mating surface.

According to another aspect of the invention, there is provided an inspection system. The inspection system includes:
  a portable inspection probe as described above; and
  an analysis module receiving the hologram of the recessed mating surface of the optical fiber connector digitally recorded by the digital holographic detection module of the portable inspection probe and numerically synthesizing at least one representation of the recessed mating surface based on the hologram thereof.

According to yet another aspect of the invention, there is provided a method for inspecting a recessed mating surface of an optical fiber connector. The method includes the steps of:
  a) digitally obtaining a hologram of the recessed mating surface; and
  b) numerically synthesizing at least one representation of the recessed mating surface of the optical fiber connector based on the hologram thereof.

Other features and advantages of the embodiments of the present invention will be better understood upon reading of preferred embodiments thereof with reference to the appended drawings.

BRIEF DESCRIPTION OF THE DRAWINGS

In FIG. 2A, the portable inspection probe includes a rigid probe tip connected thereto. In FIG. 2B, the portable inspection probe is configured to be used with a rigid probe tip connectable thereto. In FIG. 2C, the portable inspection probe is provided with a display module. In FIG. 2D, the portable inspection is provided with an extension module.

FIG. 3 is a schematic representation of a portable inspection probe, in accordance with an embodiment, including a digital holographic detection module. FIG. 3A is an enlargement of portion 3A of FIG. 3.

FIG. 5A is an enlargement of portion 5A of FIG. 5.

DESCRIPTION OF PREFERRED EMBODIMENTS

Figures 1A, 1B:
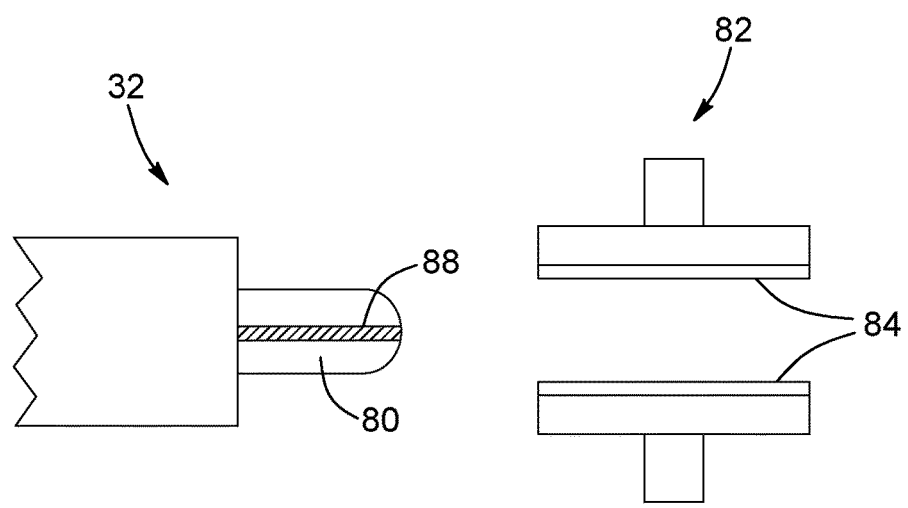
FIGS. 1A and 1B (PRIOR ART) is a schematic representation of an optical fiber mounted into a ferrule of an optical fiber connector (FIG. 1A) and of a conventional bulkhead adapter for mating the connectorized optical fiber to another optical component (FIG. 1B).

In the following description, similar features in the drawings have been given similar reference numerals, and, in order to not unduly encumber the figures, some elements may not be indicated on some figures if they were already identified in preceding figures. It should also be understood herein that the elements of the drawings are not necessarily depicted to scale, since emphasis is placed upon clearly illustrating the elements and structures of the present embodiments.

The present specification generally relates to a portable inspection probe, a system, and a method for inspecting a recessed mating surface of an optical fiber connector attached to a coupling device such as a bulkhead adapter, using digital holography.

Throughout the present specification, the term "mating surface" refers to the end portion of an optical fiber connector that, in normal use, comes in contact with another optical component. In some embodiments, the mating surface of the optical fiber connector may correspond to the endface of a ferrule, which as explained above, is understood herein to encompass both the endface of the optical fiber or fibers in the optical fiber connector and the endface of the ferrule housing the fiber. The ferrule generally protrudes from the connector body in order to be inserted into a coupling device, such as a bulkhead adapter.

The term "recessed", when used in connection with the mating surface of the optical fiber connector, refers herein to a mating surface which, from the exterior, appears to be confined in a recess, such that obtaining optical access to the mating surface for inspecting the same may not be straightforward. This situation typically occurs when the optical fiber connector is inserted into a coupling device, such as a bulkhead adapter. In this case, the "recessed mating surface" is located at or corresponds to the bottom surface of an orifice or aperture defined by a bulkhead adapter and is thus surrounded by a raised portion of the bulkhead adapter.

As mentioned above, optical fiber connectors in conjunction with coupling devices (e.g. bulkhead adapters), are typically used in optical fiber networks to mate and provide optical continuity between two optical fibers, with minimal losses and without requiring splicing. It will be understood by one of ordinary skill in the art that embodiments are not limited by the types of optical fiber connectors that can be inspected, which may include a variety of ferrule designs, sizes, shapes and polishes.

Advantageously, some embodiments are field portable and may thus provide an efficient and convenient way of inspection of the mating surface of an optical fiber connector. As used herein, the term "inspection" generally refers to an optical inspection of the mating surface of an optical fiber connector that involves digitally recording a hologram of the mating surface. In particular, the term "inspection" may further include but is not limited to measuring, analyzing and assessing information pertaining to the presence of defects and contaminants on the mating surface. It will be understood that in some embodiments, the information measured and optionally processed by the portable inspection probe may need to be interpreted by a user in order to assess the surface quality and cleanliness of the mating surface under inspection. Furthermore, embodiments may allow inspection of optical connectors in various environments, including "central office" locations in an optical network, other access points in a field-deployed network, manufacturing facilities for network equipment, research and development laboratories, and the like.

Further advantageously, as will be explained more fully below, some embodiments can free the operator from having to mechanically adjust the focus of the probe during the inspection, thus eliminating operator-related focus adjustment errors. Some embodiments may also provide compensation for optical aberrations present in the optical components along the path of the object and reference beams.

Digital Holography

Embodiments of the present invention generally involve digitally recording a hologram of the mating surface. As used herein, the term "hologram" is intended to refer to a spatially-dependent optical-intensity modulation pattern resulting from the constructive and destructive interferences between two coherent beams of light, a first beam termed the object beam emanating or reflected from an object under test and a second beam termed the reference beam. It will be understood that in some embodiments, the "object" whose hologram is to be digitally recorded generally corresponds to the mating surface of an optical fiber connector which is to be inspected. Hence, throughout this specification, the term "object" and "mating surface" may, in some instances, be used interchangeably.

In digital holography, a digital recorder, comprising a detector array and associated electronics, can be used to record the hologram, instead of a photographic plate or any other media whose optical properties are sensitive to light intensity used in conventional holography. More specifically, the reference beam and the object beam produce, at a holographic detection plane defined by the detector array, a hologram with a two-dimensional intensity distribution, which the digital recorder records and stores as digital data.

In the embodiments, the reference and object beams are combined on the detector array at a mutual non-zero angle, in what is known as spatial heterodyne detection. As a result, the hologram exhibits a fringe pattern whose spatial frequency depends on the value of this non-zero mutual angle, and contains all the information about the amplitude and phase of the object beam reflected by the mating surface under inspection. At the holographic detection plane xy0, the digitally recorded hologram can be expressed as:

$$I(x, y) = |U(x, y) + V(x, y)|^2 \qquad (1)$$

$$= \underbrace{|U(x, y)|^2 + |V(x, y)|^2}_{\text{Zero-order band}} + \underbrace{U(x, y) \cdot V^*(x, y)}_{\text{Side band}} + \underbrace{U^*(x, y)V(x, y)}_{\substack{\text{Complex conjugate} \\ \text{side band}}},$$

where $U(x, y)$ is the complex amplitude of the object beam reflected by the mating surface, $V(x, y)$ is the complex amplitude of the reference beam, and * denotes the complex conjugate of a complex quantity. The third term on the right hand side of Eq. (1) is modulated by the complex conjugate of the reference beam $V^*(x, y)$ and contains information about the complex wave field U(x, y) propagated after illuminating the object. Hence, assuming that the complex amplitude V(x, y) of the reference beam is known, either a priori from theoretical considerations or by means of a calibration procedure, the complex object wave field U(x, y) may be retrieved from the digitally recorded hologram described by Eq. (1).

It will be understood that digital holography may have several advantages over imaging methods used in conventional inspection probes employing a LED light source for illuminating the connector and a digital camera for capturing images. For example, as known in the art, an advantage of holographic techniques is that the acquisition of a single hologram allows, in theory, the simultaneous retrieval of both the amplitude and phase components of the wavefront of the object beam reflected by the object. In contrast, conventional imaging techniques are limited to recording spatially-dependent optical power information. In particular, because the phase is directly related to the wavelength and optical path length, digital holography may be capable of measuring with greater accuracy the shape and size of features, such as defects and foreign particles on the mating surface of optical fiber connectors.

Portable Inspection Probe

According to an aspect of the present specification, there is provided a portable inspection probe 20 for the inspection of a mating surface of an optical fiber connector, the mating surface being recessed with respect to an orifice in a coupling device, such as a bulkhead adapter, into which the optical fiber connector is attached. Exemplary embodiments of this aspect are shown in FIGS. 2A to 2D.

Throughout the present specification, the term "portable" is understood to refer to an inspection probe that is both compact and light enough to be readily held in, moved and operated by one or both hands of a user. In particular, the inspection probe according to some embodiments may allow portable field-testing in optical networks, including in high-density patch panels.

Broadly described, the portable inspection probe 20 includes a digital holographic detection module 22 operable to digitally record a hologram of the mating surface of the optical fiber connector. In some embodiments, such as in FIG. 2A, the portable inspection probe 20 may include a rigid probe tip 24 configured to be optically coupled to the digital holographic detection module 22 and shaped to provide optical access to the mating surface. Alternatively, in other embodiments, such as in FIG. 2B, the portable inspection probe 20 need not include a rigid probe tip itself but may rather be configured to be used with a rigid probe tip 24 connectable thereto and shaped to provide optical access to the mating surface.

The portable inspection probe 20 may also include a portable housing 26 accommodating the digital holographic detection module 22. The portable housing 26 may have an ergonomic shape to facilitate grasping and holding of the portable inspection probe 20 in the hand or hands of a user while in use, and made of lightweight yet sturdy material, for example molded plastic. Optionally, the portable inspection probe 20 may include an analysis module 28 operable to numerically synthesize at least one representation of the mating surface of the optical fiber connector based on the hologram thereof. In such cases, the portable inspection probe may also include a display module 30 (see FIG. 2C) displaying one of the at least one representation of the mating surface numerically synthesized by the analysis module 28.

Various non-limitative configurations for the optical components, embodying the portable inspection probe 20, including the digital holographic detection module 22, will now be described hereinbelow, with reference to FIGS. 3 to 6.

Digital Holographic Detection Module

Referring now to FIGS. 3 and 3A there is provided a portable inspection probe 20, which in the illustrated embodiment is adapted to inspect a 2.5 mm diameter UPC ferrule connector 32.

The portable inspection probe 20 according to some embodiments may include a digital holographic detection module 22, which may be received inside the portable housing 26 of the portable inspection probe 20, as exemplified in FIGS. 2A to 2D. The digital holographic detection module 22 may be embodied by a plurality of optical components which together are operable to digitally record a hologram of a mating surface 34 of the optical fiber connector 32 under inspection.

As mentioned above, throughout this specification, the mating surface 34 to be inspected corresponds to the object whose hologram is to be digitally recorded by the digital holographic detection module 22. In the illustrated embodiment, the mating surface 34 corresponds to the endface of a ferrule protruding from the end portion of the optical fiber connector 32, the latter being inserted into a coupling device embodied by a bulkhead adapter 82, and encompasses the endface of the optical fiber 88.

As shown in FIGS. 3 and 3A, the digital holographic detection module 22 is configured to propagate an object beam 36 and a reference beam 38 along respective object and reference optical paths 40 and 42. More specifically, the digital holographic detection module 22 may be configured to direct the object beam 36 and the reference beam 38 to interfere at a holographic detection plane 44, thereby forming the hologram of the mating surface 34.

As used herein, the term "reference beam" is intended to refer to a light beam that usually has known amplitude and phase information associated with it, for example a uniform wavefront. In contrast, the term "object beam" is intended to refer to the light beam which is first used to illuminate the object under inspection and then reflected by the illuminated object, therefore containing amplitude and phase information from the object. The object beam reflected by the object is subsequently made to interfere with the reference beam and form the hologram of the mating surface at the holographic detection plane, which is digitally recorded by the digital holographic detection module.

The digital holographic detection module 22 of the portable inspection probe 20 shown in FIGS. 3 and 3A may include a light source assembly 46 configured to generate the object and reference beams 36 and 38. The light source assembly 46 may include a coherent light source 48 configured to generate a coherent source beam 50 and a first beam splitter 52 configured to split the coherent source beam 50 into the object beam 36 and the reference beam 38. The coherent light source 48 can be embodied by any appropriate device or combination of devices able to generate a source beam 50, and object and reference beams 36 and 38, of sufficiently high spatial and temporal coherence that is suitable for digital holography imaging. Preferably, the coherent light source 48 is a laser source, whose emission is both longitudinally (i.e. spectrally, in the optical frequency domain) and transversally (i.e. spatially) single mode.

In one example, the coherent source beam 50 emitted by the coherent light source 48 may be incident on the first beam splitter 52, where a part of the coherent source beam 50 is transmitted through the first beam splitter 52 and the remaining part of the coherent source beam 50 is specularly reflected by the first beam splitter 52. The first beam splitter 52 can be, for example, fifty-percent reflective and can be embodied by a plate beam splitter, a beam sampler, a pellicle beam splitter, a beam splitter cube, a wedge or the like.

In the illustrated embodiment, the parts of the coherent source beam 50 that are transmitted through and specularly reflected by the first beam splitter 52 respectively form the reference beam 38 and the object beam 36. However, in other embodiments, the first beam splitter 52 may transmit a part of the coherent source beam 50 to form the object beam 36 and specularly reflect the remaining part of the coherent source beam 50 to form the reference beam 38 without departing from the scope of the present specification.

The propagation of the object and reference beams 36 and 38 along the respective object and reference optical paths 40 and 42 during the inspection of the mating surface 34 of the optical fiber connector 32 will now be described hereinbelow with continuing reference to FIGS. 3 and 3A.

After specular reflection by the first beam splitter 52, the object beam 36 may traverse an illumination lens assembly 54 and be specularly reflected by an illumination mirror 56 onto a second beam splitter 58. The first beam splitter 52 can be, for example, fifty-percent reflective and can be embodied by a plate beam splitter, a beam sampler, a pellicle beam splitter, a beam-splitter cube, a wedge or the like.

It is to be noted that throughout the present specification, the term "lens assembly" in reference to the illumination lens assembly or to other subsequently introduced lens assemblies may include a single lens or it may include a plurality of lenses depending on the overall design of the lens assembly. The term "lens assembly" may include lenses of optical glasses or any other optical components for altering the path of light. In the illustrated embodiment, the illumination lens assembly 54, as well as the other lens assemblies described below, includes a triplet lens such a Hastings triplet lens which, as known in the art, introduces minimal optical aberration. In addition, it will be understood by one of ordinary skill in the art that in embodiments where reference and object beams having a high coherence are used, using flat or low-curvature lenses may not be optimal since such lenses may generate an unacceptable degree of residual reflections, even if antireflection coatings are used. In this regard, common triplet lenses are generally made of singles lenses having sufficiently high curvature to avoid or at least mitigate the effects of such residual reflections. Furthermore, in some embodiments, an anti-reflective coating may be provided on the various lenses provided in the portable inspection probe 20 to further reduce such undesirable residual reflections.

In the illustrated embodiment, a part of the object beam 36 incident on the second beam splitter 58 is reflected by the same onto a probing optical assembly 60 of the portable inspection probe 20. The probing optical assembly 60 is configured to direct the object beam 36 onto the mating surface 34 of the optical fiber connector 32 and to collect the object beam 36 upon reflection thereof by the mating surface 34 during the inspection thereof. The probing optical assembly 60 is provided in the object optical path 40 and is not traversed by the reference beam 38.

In FIGS. 3 and 3A, the probing optical assembly 60 is embodied by a triplet lens (e.g. Hastings triplet lens). In this embodiment, the probing optical assembly 60 is configured and positioned so as to focus the object beam 36 slightly behind the mating surface 34 of the optical fiber, thereby ensuring illumination of the mating surface under inspection.

In the embodiment of FIGS. 3 and 3A, the probing optical assembly 60 corresponds to a component of the digital holographic detection module 22, which may be included inside the portable housing of the portable inspection probe 20 (see FIGS. 2A to 2D). However, in other embodiments, the probing optical assembly 60, in whole or in part, may be provided inside the rigid probe tip 24 connected to or to be used with the portable inspection probe 20 without departing from the scope of the specification.

A part of the object beam 36 reflected by the mating surface travels back through the probing optical assembly 60 and onto the second beam splitter 58, through which it is transmitted to then impinge upon a beam combiner 64. A part of the object beam 36 is then specularly reflected by the beam combiner 64 toward a detector array 66 positioned at the holographic detection plane 44.

Meanwhile, after transmission through the first beam splitter 52 the reference beam 38 may traverse collimation optics 68 provided in the digital holographic detection module 22 and along the reference optical path 42. The collimation optics 68 is configured to at least approximately collimate the reference beam 38 before interference with the object beam 36. In the illustrated embodiment, the collimation optics 68 includes a reference lens assembly 70 embodied by a triplet lens (e.g. Hastings triplet lens). The reference beam 38 may traverse the reference lens assembly 70 and be transmitted by the beam combiner 64 toward the detector array 66.

As can be seen from FIGS. 3 and 3A, the beam combiner 64 may be positioned at the juncture of the object and reference optical paths 40 and 42, so as to combine and direct the reference and object beams 36 and 38 to interfere at the holographic detection plane 44. The beam combiner may be embodied by a plate beam splitter, a beam sampler, a pellicle beam splitter, a beam-splitter cube, a wedge or the like.

The object beam 36 and the reference beam 38 emerging from the beam combiner 64 are superposed so as to mutually interfere on the detector array 66. In order to ensure spatial heterodyne detection, the angle of the beam combiner 64 with respect to the object and reference optical paths is adjusted so that the reference beam 38 and the object beam 36 reflected from the mating surface 34 under inspection meet at the holographic detection plane 44 at a non-zero mutual angle.

It will be understood by one of ordinary skill in the art that this angle is preferably sufficiently large to separate the positive spatial frequencies from the corresponding negative spatial frequencies (i.e. complex conjugate) of the signal detected by the detector array 66, yet small enough so as not to be filtered by the pixel size of the detector array. For example, a suitable value could be slightly larger than the numerical aperture of the object beam 36 divided by the magnification introduced by the probing optical assembly 60, and a corresponding suitable value for the pixel aperture could be twice this angle.

The detector array 66 may comprise an optical-power sensitive detector, which in conjunction with appropriate electronics, is capable of recording, in a digital form, the hologram of the mating surface 34, that is, the intensity modulation pattern or interferogram resulting from the superposition and interference of the object and reference beams 36 and 38. As one skilled in the art will understand, the detector array 66 can be embodied by an optical power-sensitive image detector having adequate responsivity to the wavelength emitted by the coherent light source 48, for example as may be employed in a digital camera or any similar digital device or recorder having a two-dimensional array of light-sensitive pixels. In preferred embodiments, the detector array 66 is a two-dimensional CCD-based or a CMOS-based detector array, but one-dimensional detector arrays or other types of two-dimensional detector arrays could be used in other embodiments.

It is to be noted that it is a feature of some embodiments to minimize the number of specular reflections experienced by the reference beam 38 before reaching the detector array 66. Indeed, because inexpensive highly-coherent laser sources are now readily available, it has become less critical for the length of the reference optical path 42 to be approximately equal to the length of the object optical path 40, which has been considered traditionally to be a requirement for holography. By relaxing this constraint, it may be possible to minimize the number of specular reflections undergone by the reference beam 38 and to shorten the length of the reference optical path 42, thereby preserving a high-quality reference beam 38 while allowing the overall size of the digital holographic detection module 22 to be reduced.

Rigid Probe Tip

Referring more specifically to FIGS. 2A to 2D, 3, 3A and 6, the portable inspection probe 20 according to some embodiments may also include or may be used with a rigid probe tip 24. As mentioned above, the rigid probe tip 24 is configured to be optically coupled to the digital holographic detection module 22 and shaped to provide optical access to the mating surface 34 during the inspection thereof.

Figure 2A:
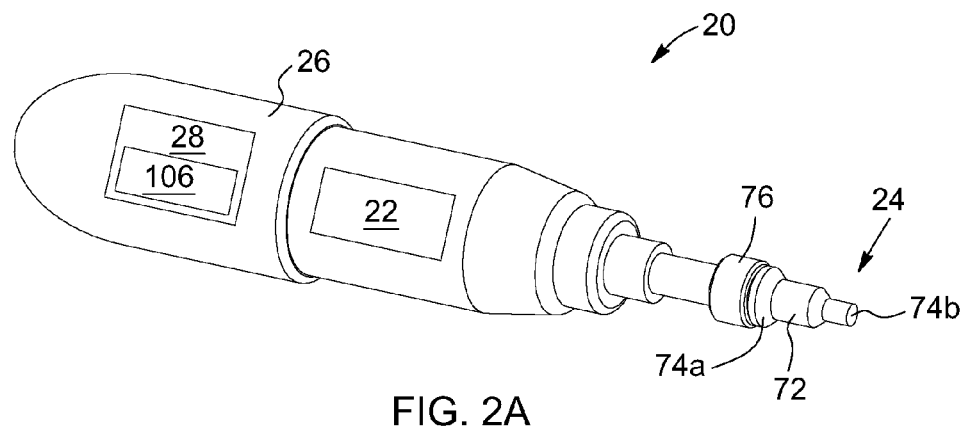
FIGS. 2A to 2D are schematic representations of a portable inspection probe, in accordance with two embodiments.
Figure 2B:
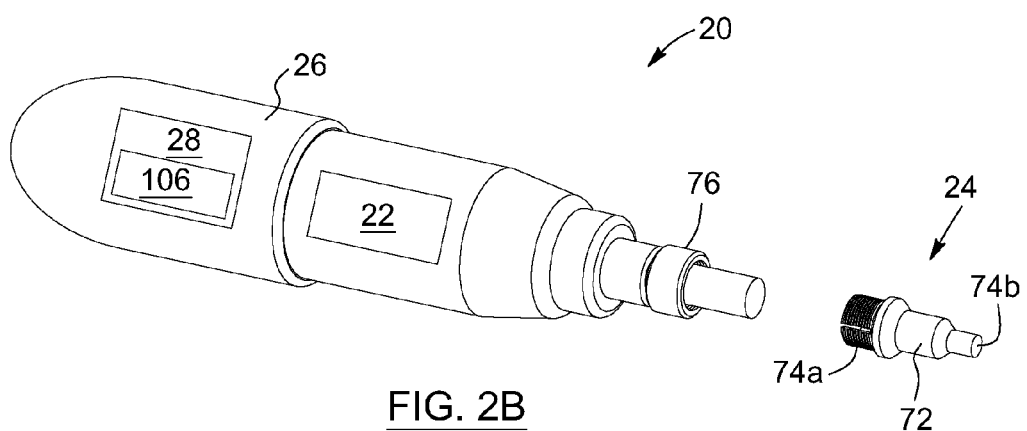
Figure 2C:
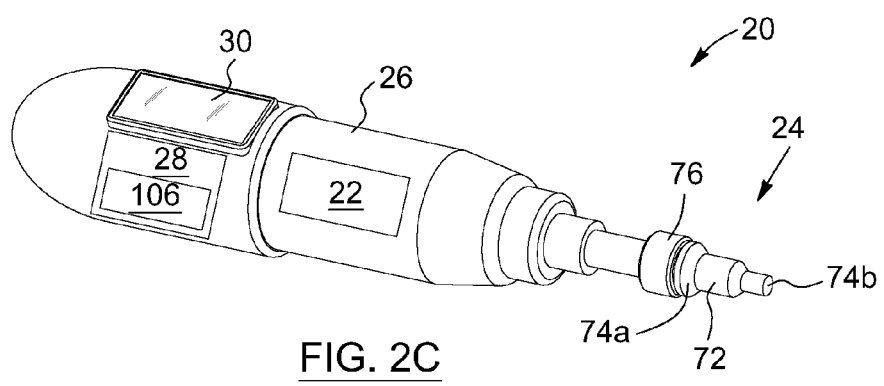
Figure 6:
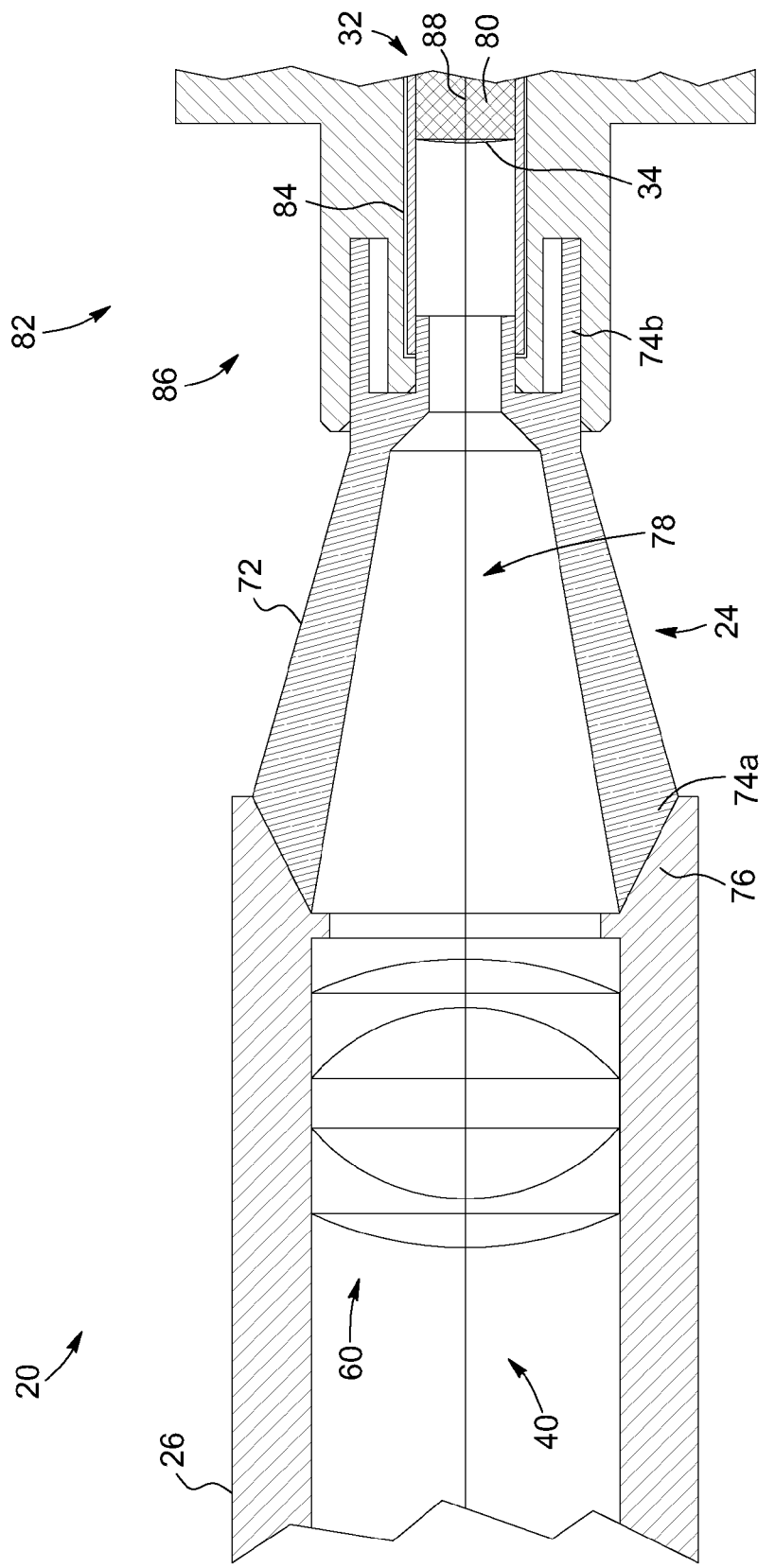
FIG. 6 is a schematic representation of a rigid probe tip connected to or to be used with the portable inspection probe, in accordance with an embodiment. The rigid probe tip is optically coupled to a digital holographic detection module for providing optical access to the recessed mating surface of an optical fiber connector.

More specifically, the rigid probe tip 24 may have an elongated body 72 extending between proximal and distal ends 74a, 74b. As shown in FIGS. 2A and 2B, the proximal end 74a may be connectable to a tip connector 76 provided on the portable housing 26 of the portable inspection probe 20, while the distal end 74b may be insertable into the optical fiber connector 32 so as to be in a close proximity to the mating surface 34 during the inspection thereof. The elongated body 72 may define a tip optical path 78 that coincides with a portion of the object optical path 40 and that enables the object beam 36 to propagate bi-directionally between the digital holographic detection module 22 and the mating surface 34. In the embodiments of FIGS. 3, 3A and 6, the mating surface 34 corresponds to the endface of an optical fiber ferrule 80.

As will be understood by one of ordinary skill in art, proper inspection of the recessed mating surface 34 of an optical fiber connector 32 inserted into a bulkhead connector 82 generally involves adequate position and orientation of the portable inspection probe 20 with respect to the mating surface 34 to be inspected. To this end, the portable inspection probe 20 may include or may be adapted for use with a rigid probe tip 24 so as to provide an optimal path for light to propagate between the digital holographic detection module 22 and the mating surface 34 of an optical connector 32 to be inspected. In some embodiments, a specific type of rigid probe tips 24 may be provided for each type of optical fiber connector 32 and/or optical coupler such as a bulkhead connector to be inspected.

It will be understood that the rigid probe tip 24 may be composed of a sufficiently strong and sturdy material such as stainless steel, nickel or the like to avoid corrosion as well as to provide rigidity. The rigid probe tip 24 may be hollow or incorporate therein one or more optical components such as a lens assembly or a window. The design of the rigid probe tip may be optimized for a particular mating surface (e.g. APC connector endface) attached to the opposing opening in the bulkhead adapter 82 and may additionally or alternatively serve to extend the reach of the portable inspection probe 20. The distal end 74b of the rigid probe tip 24 is preferably suitably sized and shaped for insertion into an optical fiber connector bulkhead adapter 82.

It should also be appreciated that, as used herein, the term "rigid" when referring to the probe tip 24 is intended to mean that the probe tip is self-supporting and maintains its shape and does not exhibit significant deformation under conditions of normal usage of the portable inspection probe, such that optical continuity of the object path 40 is maintained during the holographic acquisition process. Consequently, it may be envisaged that the tip comprise a material such as hard rubber or other material that retains its shape during normal use.

It is to be noted that, although the rigid probe tip 24 is preferably connected to the tip connector 76 of the portable housing 26 in a rigid fashion during the inspection of the mating surface 34, the rigid probe tip 24 may advantageously be connected to the portable housing 26 in a releasable or detachable manner.

Such a mechanism for releasable or detachable connection between the rigid probe tip 24 and the portable housing 26 may comprise a magnetic "quick connect" or functional equivalent, analogous to that taught in U.S. Pat. No. 7,264,479 to Lee, which automatically releases the rigid probe tip 24 from the rest of the inspection probe 20 whenever, with the rigid probe tip 24 inserted into an orifice such as an optical fiber connector bulkhead adapter 82, the inspection probe 20 is subjected to a couple exceeding a given threshold defined by the strength of the magnetic coupling between the rigid probe tip 24 and the portable housing 26.

For example, the magnetic mechanism for releasable or detachable connection may comprise a permanent magnet in physical contact or otherwise magnetically coupled to the tip connector 76 which is made of a magnetic material. The proximal end 74a of the rigid probe tip 24 is also made of a magnetic material and upon connection to the tip connector 76 by physical contact, the magnetic field generated by the magnet holds the rigid probe tip 24 in place. The tip connector 76 and the proximal end 74a may also comprise complementary alignment features, such as complementary frustoconical shapes, to properly align the tip optical path 78 to coincide with the object optical path 40 when connected. However, the complementary alignment features are designed such that they allow disconnection of the rigid probe tip 24 upon subjection to a disconnecting couple between the rigid probe tip 24 and the portable housing 26.

It will be readily understood that although the rigid probe tip 24 illustrated schematically in the embodiment of FIG. 6 also has a frustoconical shape converging from the proximal end 74a to the distal end 74b thereof, the shape of the rigid probe tip 24 need not possess the same geometrical configuration in other embodiments and may vary according to the type of optical fiber connector 32 being inspected. Moreover, in some embodiments, the portable inspection probe 20 may be provided with a plurality of easily interchangeable rigid probe tips 24, each of which being adapted for the inspection of one specific type of optical fiber connector 32.

It will be understood that the portable inspection probe 20 need not be not limited by the type of optical fiber connector 32 that can be inspected, which may include single-fiber and multi-fiber connectors of various types such as SMA 906, ST, Biconic, FC, HMS-10, SC, FDDI, ESCON, EC/RACE, LC, MT, MT-RJ, MTP, E-2000. Furthermore, embodiments are not limited by the inspection environment, which may include patchcord inspection and patch-panel bulkhead inspection, by the polish style, which may include physical contact (PC), ultra physical contact (UPC) and angled physical contact (APC), or by the diameter of the connector ferrules, for which may be equal to 1.25 mm or 2.5 mm.

A bulkhead adapter 82 may be provided to facilitate optical access to the ferrule 80, as illustrated in FIG. 3A. The bulkhead adapter 82 may consist of a dual female coupling device within which an alignment sleeve 84 allows precise alignment of the ferrule 80. As is well known in the art, bulkhead adapters are typically used to mate a male connector ferrule to another male connector ferrule, a transmitter or a receiver. Of course, one of ordinary skill in the art will understand that embodiments are limited by the presence, design and configuration of the bulkhead adapter 82.

In the embodiment shown in FIG. 3 and more clearly seen in the enlarged portion thereof shown in FIG. 3A, the rigid probe tip 24 connected to the tip connector 76 of the portable housing 26 and optically coupled to the digital holographic detection module 22, such as shown in FIG. 6, may be inserted through a first port 86 of the dual female bulkhead adapter 82, while the ferrule 80 containing the optical fiber 88 may be connected to a second port 90 of the bulkhead adapter 82. The rigid probe tip 24 may thus provide optical access to the fiber endface to the object beam 36 emerging from the probing optical assembly 60.

It is an advantage of embodiments of the present specification that the inspection of the mating surface 34 of an optical fiber connector 32 may be conveniently performed while the ferrule 80 housing the optical fiber 88 is inserted into a bulkhead adapter 82, thus avoiding the need to disconnect the optical fiber connector 32 from the bulkhead adapter 82 prior to the inspection of the mating surface 34. Furthermore, it will be understood that the inspection process may be further facilitated by the fact that, when the optical fiber connector 32 is attached to the bulkhead adapter 82, the ferrule 80 is held in a fixed position therein. Alternatively or additionally, the rigid probe tip 24 included in or intended to be used with the portable inspection probe 20 may be designed such that the male connector ferrule may be directly inserted therein, that is, without the need for an intervening bulkhead adapter.

By way of example, FIGS. 2D, 4, 5 and 5A illustrate further non-limiting variants of the portable inspection probe 20 according to some embodiments.

Figure 2D:
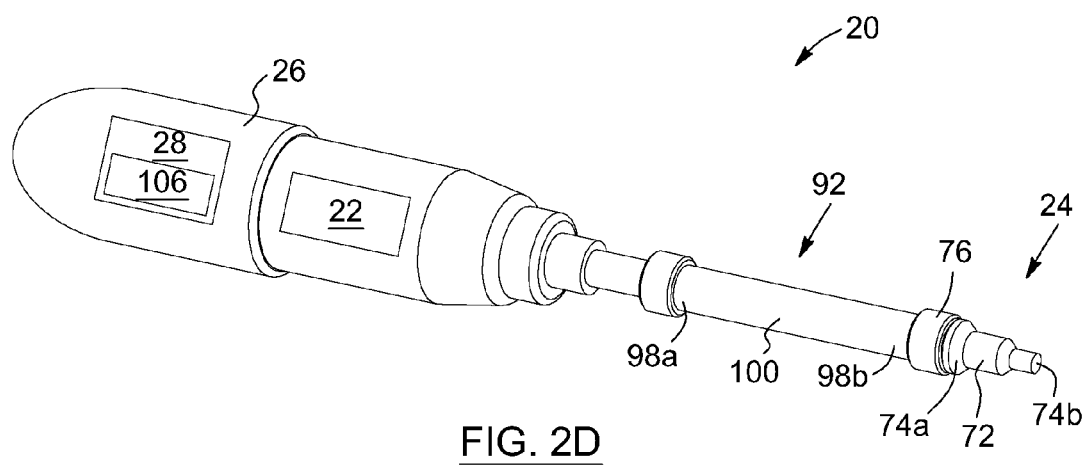
Figure 4:
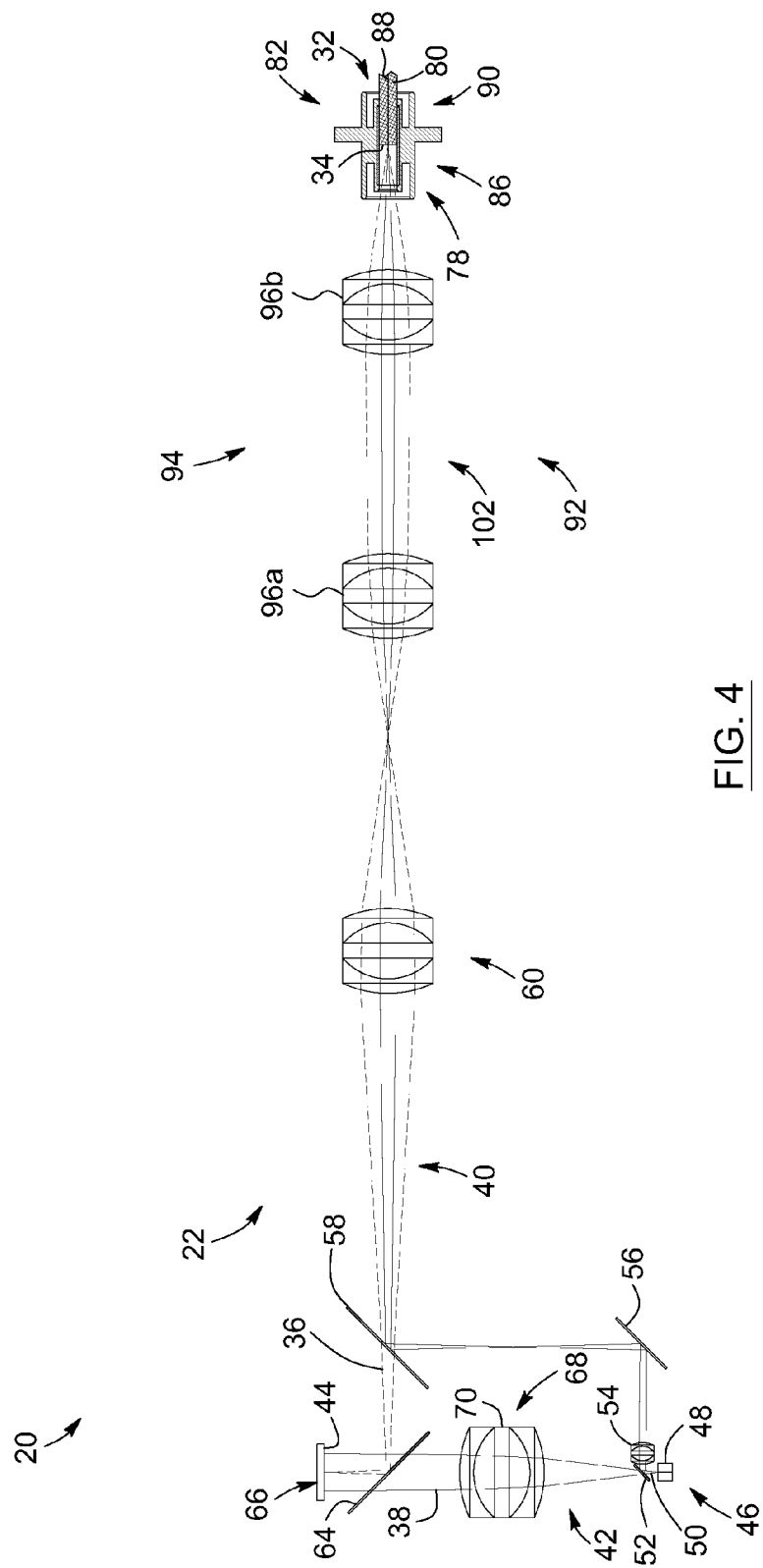
FIG. 4 is a schematic representation of a portable inspection probe, in accordance with an embodiment, including a digital holographic detection module and an extension module.

Referring now to FIGS. 2D and 4, there is provided an embodiment of a portable inspection probe 20 including an extension module 92. The extension module 92 may have an extension lens assembly 94 including spaced apart collimating lenses 96a, 96b configured to propagate the object beam 36 between the digital holographic detection module 22 and the mating surface 34 during inspection thereof. It will be understood that while in the illustrated embodiment the extension module 92 is provided as a distinct component of the portable inspection probe 20, in other embodiments, the extension module 92 may be provided integrally with the rigid probe tip 24 without departing from the scope of the specification. Referring to FIG. 2D, the extension module 92 may include a first end 98a connectable to the tip connector 76 of the portable housing 26, a second end 98b connectable to the proximal end 74a of the rigid probe tip 24 and an elongated body 100 that defines an optical channel 102 between the first and second ends 98a, 98b to receive the extension lens assembly 94. Advantageously, the provision of the extension module 92, which optionally may be releasably connectable to tip connector 76 of the portable housing 26, may increase the capability of the portable inspection probe 20 to inspect less accessible mating surfaces.

Figure 5:
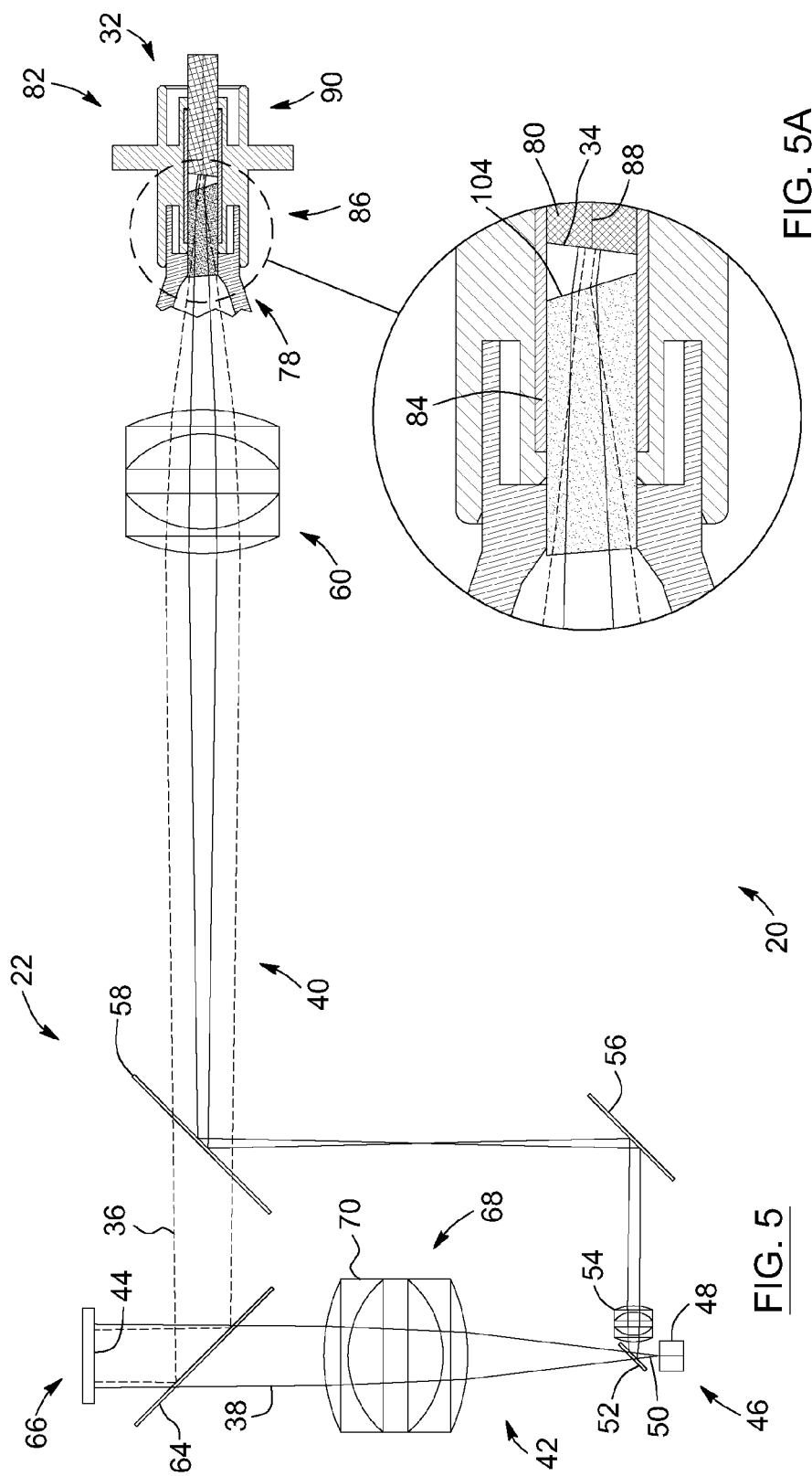
FIG. 5 is a schematic representation of a portable inspection probe, in accordance with an embodiment, adapted to inspect angle-polished optical fiber connectors.

Referring now to FIGS. 5 and 5A, there is provided another embodiment of a portable inspection probe 20, wherein the rigid probe tip 24 is adapted to the inspection of the endface of an optical fiber 88 mounted into an angled physical contact (APC) ferrule 80. As mentioned above, APC and UPC connectors differ mainly by the geometry of the mating surface 34 (e.g. the ferrule endface). The APC ferrule endface radius is polished at a modest angle, usually eight degrees, whereas the UPC ferrule endface radius is polished at an angle of zero degrees. This eight-degree angle generally improves the return loss performance of APC connectors compared to UPC connectors by causing reflected light to be absorbed by the cladding of the fiber rather than reflected back at the source. In order to take into account and compensate for this eight-degree angle when the object beam 36 is incident on the mating surface 34 including the endface of the optical fiber 88, the rigid probe tip 24 of the embodiment shown in FIGS. 5 and 5A may further include a glass rod 104 polished at an appropriate angle which inserts inside the alignment sleeve 84 of the bulkhead adapter 82.

Analysis Module

In some embodiments, the portable inspection probe 20 may further include an analysis module 28 for analyzing the digitally recorded hologram and optionally performing other processing functions, as shown in FIGS. 2A to 2D. More specifically, the analysis module 28 is operable to numerically synthesize at least one representation of the mating surface of the optical fiber connector based on the hologram thereof.

As used herein, the term "representation of the mating surface" is intended to include any image information that can be numerically retrieved from the digitally recorded hologram and be used to assess the condition of the mating surface during the inspection thereof. In particular, the term "representation of the mating surface" is used to indicate that what is numerically synthesized by the analysis module is not necessarily a magnified image of what would be seen directly by the eye looking at the mating surface, as is the case in conventional fiber inspection probes, but may include phase or amplitude imaging of the mating surface, or a combination thereof, or may simply provide a numerical value based on a predefined quality criterion, or, even more simply, may just provide a qualitative indication, such as a "pass/fail" indicator.

The analysis module 28 of the portable inspection probe 20 may be embodied by any type of appropriate processing unit capable of processing the digital holographic data recorded by the detector array. In the present specification, the term "processing unit" is understood to refer to a functional entity that controls and executes the operations required for numerically synthesizing the at least one representation of the mating surface based on the hologram thereof digitally recorded by the digital holographic detection module 22. It will be understood by one of ordinary skill in the art that the processing unit embodying the analysis module 28 may be implemented as a single unit or a plurality of interconnected processing sub-units and may be embodied by a microprocessor, a central processing unit (CPU), a microcontroller, or by any other processing resource or any combination of such processing resources configured to operate collectively as a processing unit.

It may also be envisaged that certain aspects of the processing may be performed remotely, approximately in "real time", via "cloud-based" processing.

It will also be understood that the analysis module 28 of the portable inspection probe 20 is described as a module associated with one or more different functions, in practice, the analysis module 28 may include a plurality of sub-modules, routines, components, communication ports, software and the like cooperating together in order to accomplish the corresponding function. It will be further understood that the subdivision into such modules is made from a conceptual standpoint only and that, in practice, a given hardware or software component may be common to different modules, and that components of different modules may be combined together physically and logically without departing from the scope of the present specification.

In some embodiments, the synthesizing process may be carried out numerically and may include processing the digital holographic data using conventional techniques based on the theory of light diffraction. In this regard, it will be understood by one of ordinary skill in the art that various techniques could be employed, given the many approaches and algorithms available for numerically synthesizing digitally recorded holograms.

In some embodiments, the numerically synthesized representation of the mating surface may contain information pertaining to the surface quality (e.g. defects, cracks, scratches and polish quality) and cleanliness (e.g. contaminants and foreign particles) thereof. Advantageously, the analysis module in some embodiments can detect defects or particles as small as 1 µm or less.

Referring to FIG. 2A, the analysis module 28 may include a comparison module 106 operable to characterize at least one quality criterion from the at least one representation of the mating surface numerically synthesized by the analysis module 28. For example, in some embodiments, the at least one representation may be compared against one or more pre-programmed or user-defined quality criteria to provide an indication of the number and severity of defects and foreign bodies on the mating surface (e.g. a ferrule endface) under inspection.

The results of the characterization performed by the comparison module 106 may be displayed as simple pass/fail or pass/dirty/defects indicators using, for example, differently colored LED indicators provided on the portable inspection probe 20. Alternatively or additionally, the at least one representation of the mating surface may be displayed on a display module 30 included on the portable inspection probe 20, such as in FIG. 2C, where the display module 30 is embodied by a liquid crystal display (LCD) screen. However, any other appropriate display technology such as, for example, LED technology, organic LED (OLED) technology, or active-matrix OLED (AMOLED) technology could be used in other embodiments. For example, a representation of a ferrule endface may be numerically synthesized by the analysis module 28 and on which identified defects and foreign particles are emphasized by appropriate color indicators. This representation can be processed for display by the display module 30 integrated with the portable inspection probe 20. In some embodiments, the representation may be further transmitted wirelessly to a personal computer, a tablet computer or a smartphone for viewing, storing or further processing. Real-time video display of the representation by the display module 30 may be envisaged if sufficient computational power is available.

Inspection System

Figure 7A:
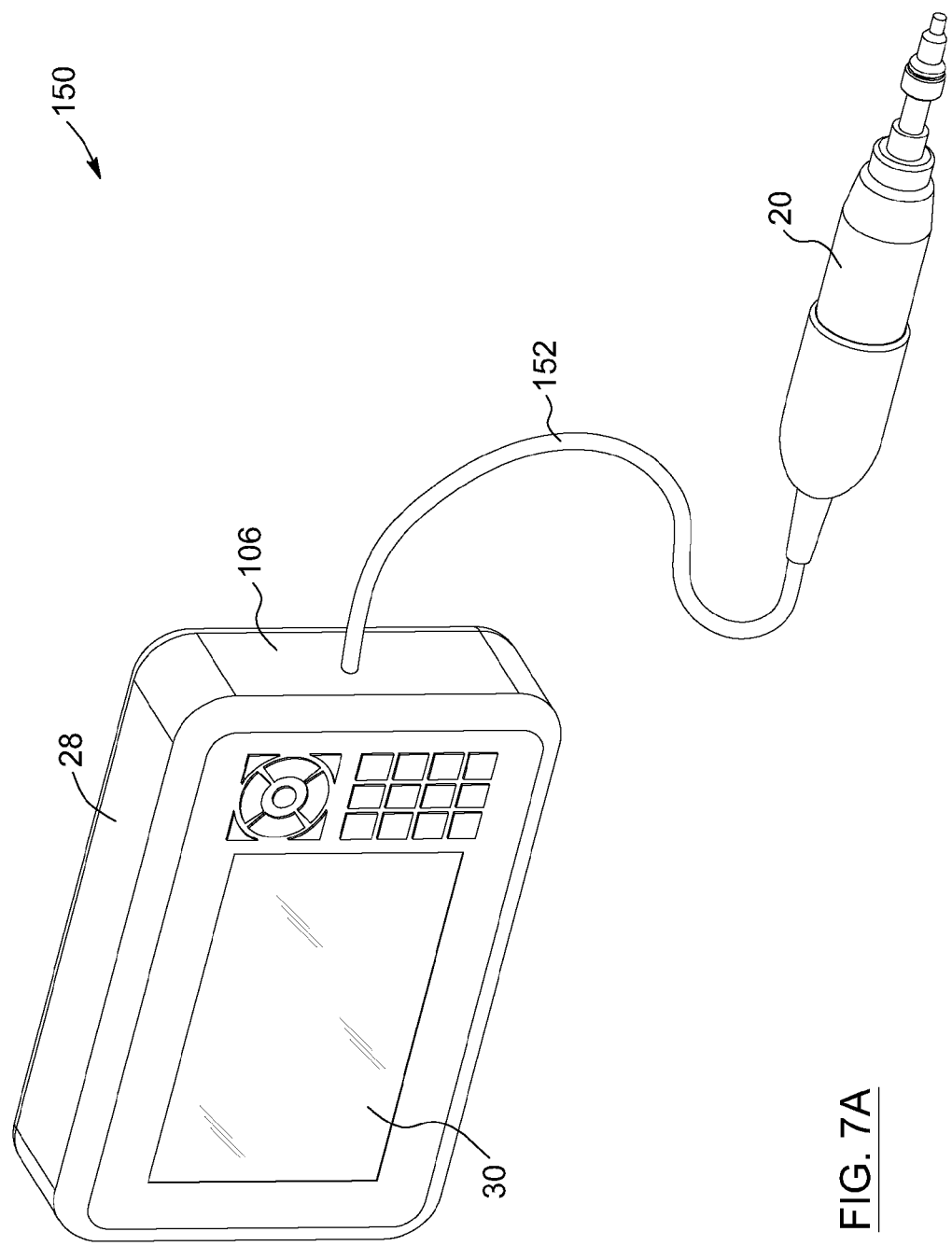
FIGS. 7A and 7B are schematic representations of an inspection system, in accordance with embodiments.
Figure 7B:
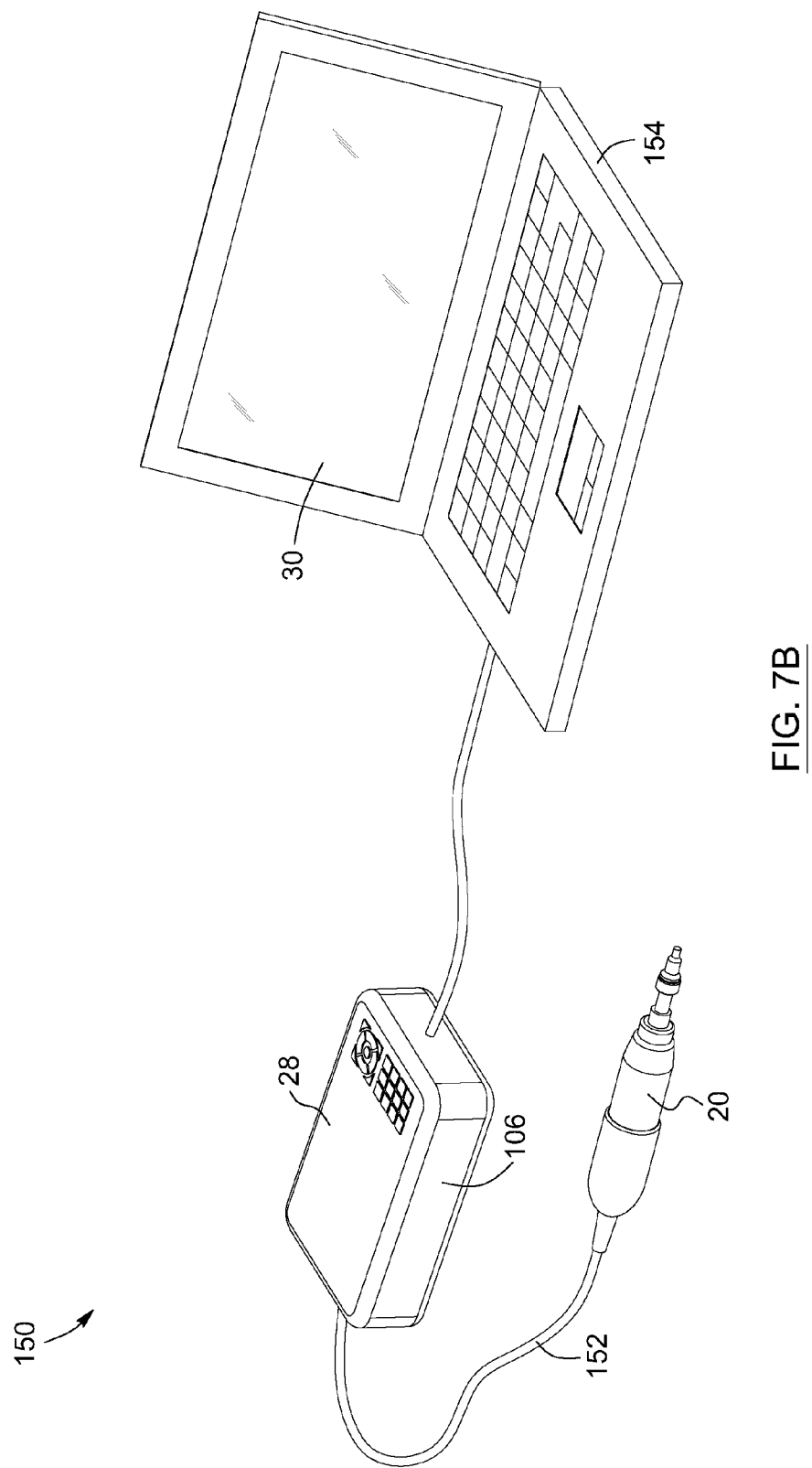

Referring now to FIGS. 7A and 7B, in accordance with another aspect of the specification, there is provided an inspection system 150. The inspection system 150 includes a portable inspection probe 20 such as described above and an analysis module 28 which, in this case, is part of a device physically distinct from the portable inspection probe 20.

The analysis module 28 of the inspection system 150 is configured to receive the hologram of the mating surface of the optical fiber connector which is digitally recorded by the digital holographic detection module 22 of the portable inspection probe 20. The analysis module 28 is also operable to numerically synthesize at least one representation of the mating surface based on the hologram thereof.

The analysis module 28 can be embodied by a computer, a microcontroller, or any by any type of appropriate processing unit capable of processing the digital holographic data recorded by the detector array. For example, in the embodiments shown in FIGS. 7A and 7B, the analysis module 28 is embodied by a portable platform which is electrically connectable to the portable inspection probe 20 by means of a wire connection 152. Alternatively or additionally, in other embodiments, a wireless connection could be established between the analysis module 28 and the portable inspection probe 20.

In some embodiments, the synthesizing process performed by the analysis module 28 of the inspection system 150 may be carried out numerically and may include processing the digital holographic data using conventional techniques based on the theory of light diffraction. In this regard, it will be understood by one of ordinary skill in the art that various techniques could be employed in some embodiments, given the many approaches and algorithms available for numerically synthesizing digitally recorded holograms.

In some embodiments, the numerically synthesized representation of the mating surface may contain information pertaining to the surface quality (e.g. defects, cracks, scratches and polish quality) and cleanliness (e.g. contaminants and foreign particles) thereof. Advantageously, the analysis module in some embodiments can detect defects or particles as small as 1 µm or less.

Still referring to FIGS. 7A and 7B, and similarly to the analysis module of the portable inspection probe described above, the analysis module 28 of the inspection system 20 may include a comparison module 106 operable to characterize at least one quality criterion from the at least one representation of the mating surface numerically synthesized by the analysis module 28. For example, in some embodiments, the at least one representation may be compared against one or more pre-programmed or user-defined quality criteria to provide an indication of the number and severity of defects and foreign bodies on the mating surface (e.g. a ferrule endface) under inspection.

The results of the characterization performed by the comparison module 106 may be displayed as simple pass/fail or pass/dirty/defects indicators using, for example, differently colored LED indicators provided on the portable inspection probe 20. Alternatively or additionally, the at least one representation of the mating surface may be processed for display on a display module 30 integrated with the analysis module, such as in FIG. 7A, on the display of a personal computer 154 connected via a cable the analysis module 28, such as in FIG. 7B, on the screen of a handheld monitor, or on any other appropriate viewing device. For example, a representation of a ferrule endface may be numerically synthesized by the analysis module 28, and identified defects and foreign particles may be highlighted on this representation by appropriate color indicators. This representation can be processed for display by the display module 30 integrated with the analysis module 28. As described above in respect to the portable inspection probe 20, the representation synthesized by the analysis module 28 of the inspection system 150 may further be transmitted wirelessly to a personal computer, a tablet computer or a smartphone for viewing, storing or further processing. Real-time video display of the representation by the display module 30 may be envisioned if sufficient computational power is available.

Inspection Method

Figure 8A:
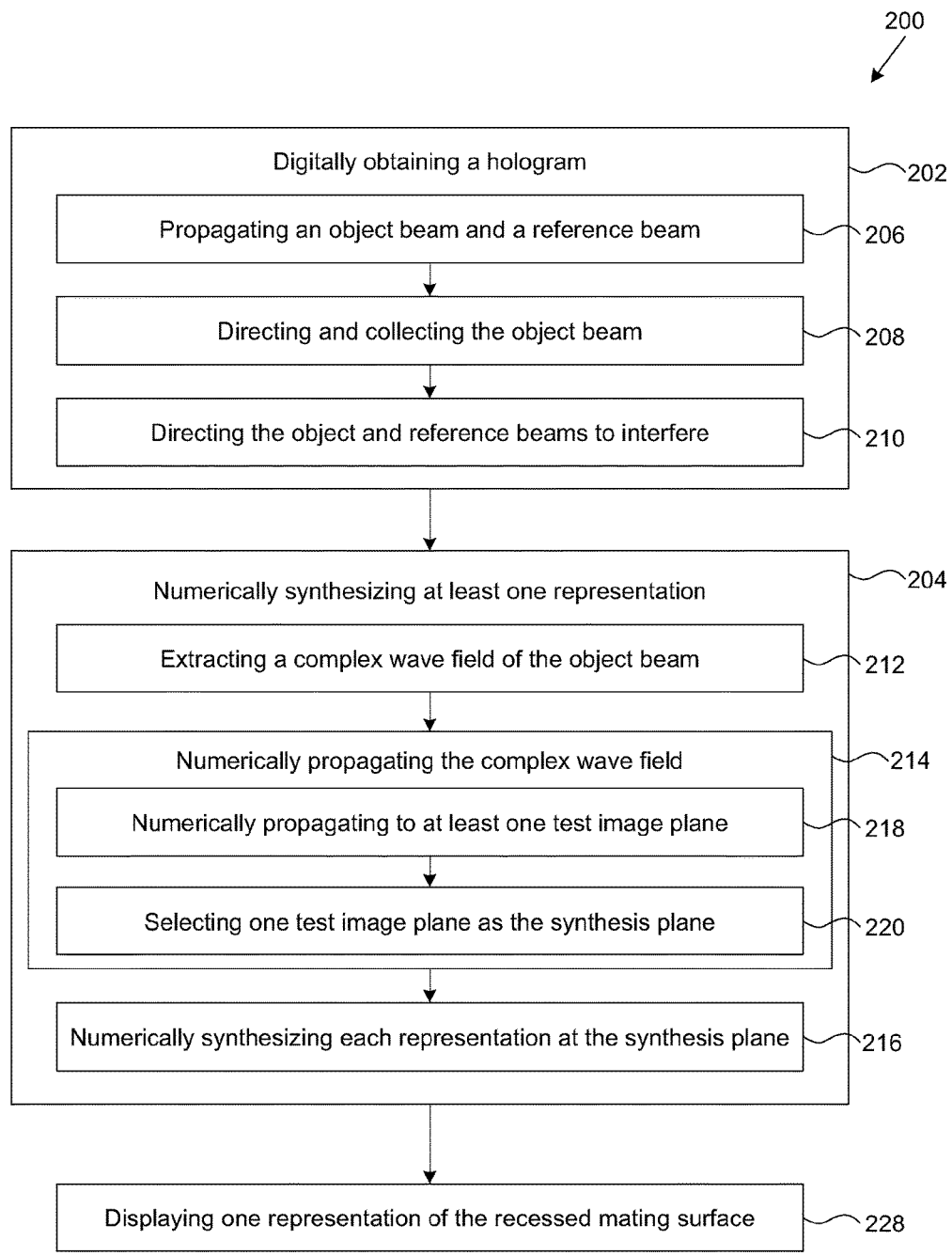
FIGS. 8A to 8C are flow charts of a method for inspecting a recessed mating surface of an optical fiber connector, in accordance with embodiments.
Figure 8B:
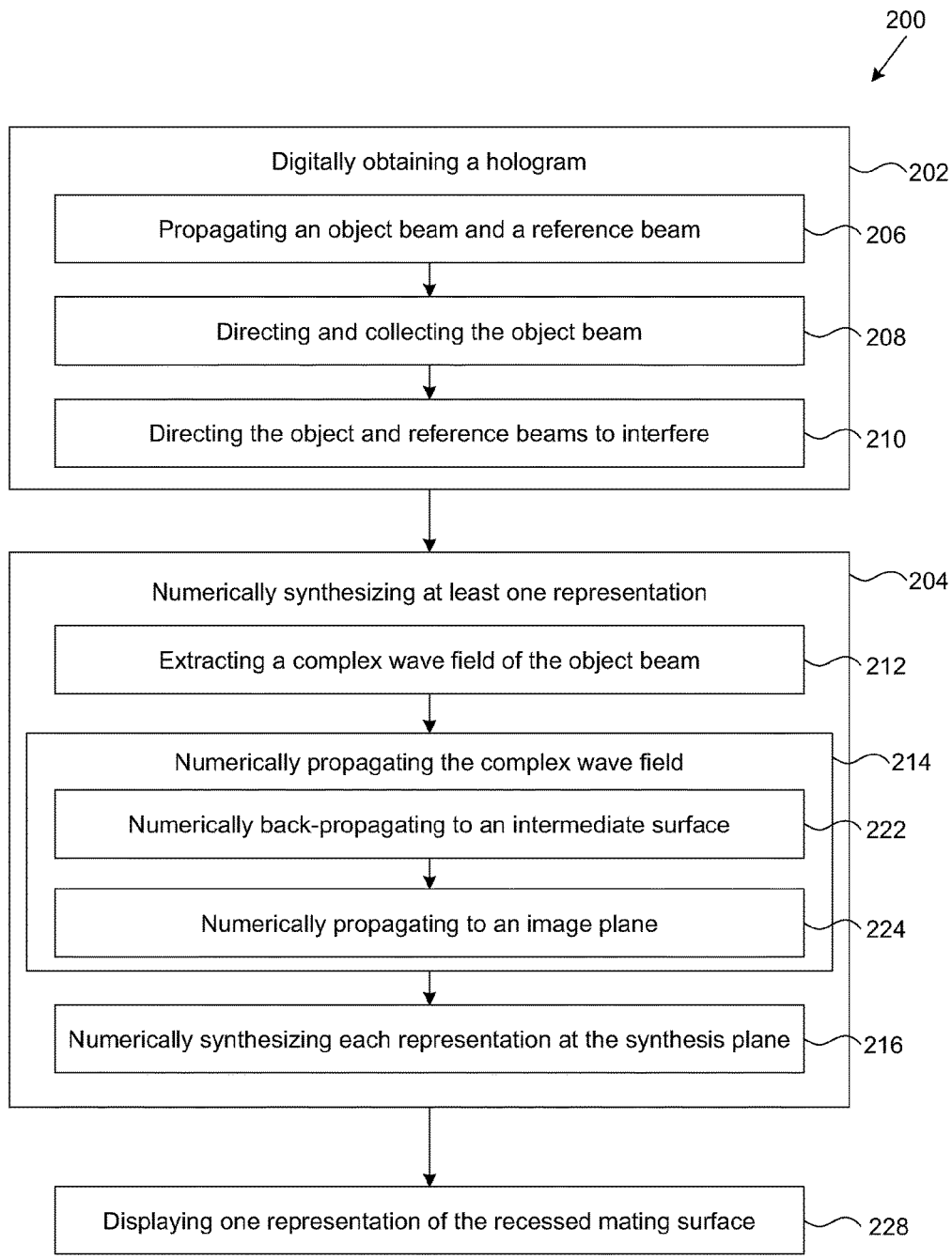
Figure 8C:
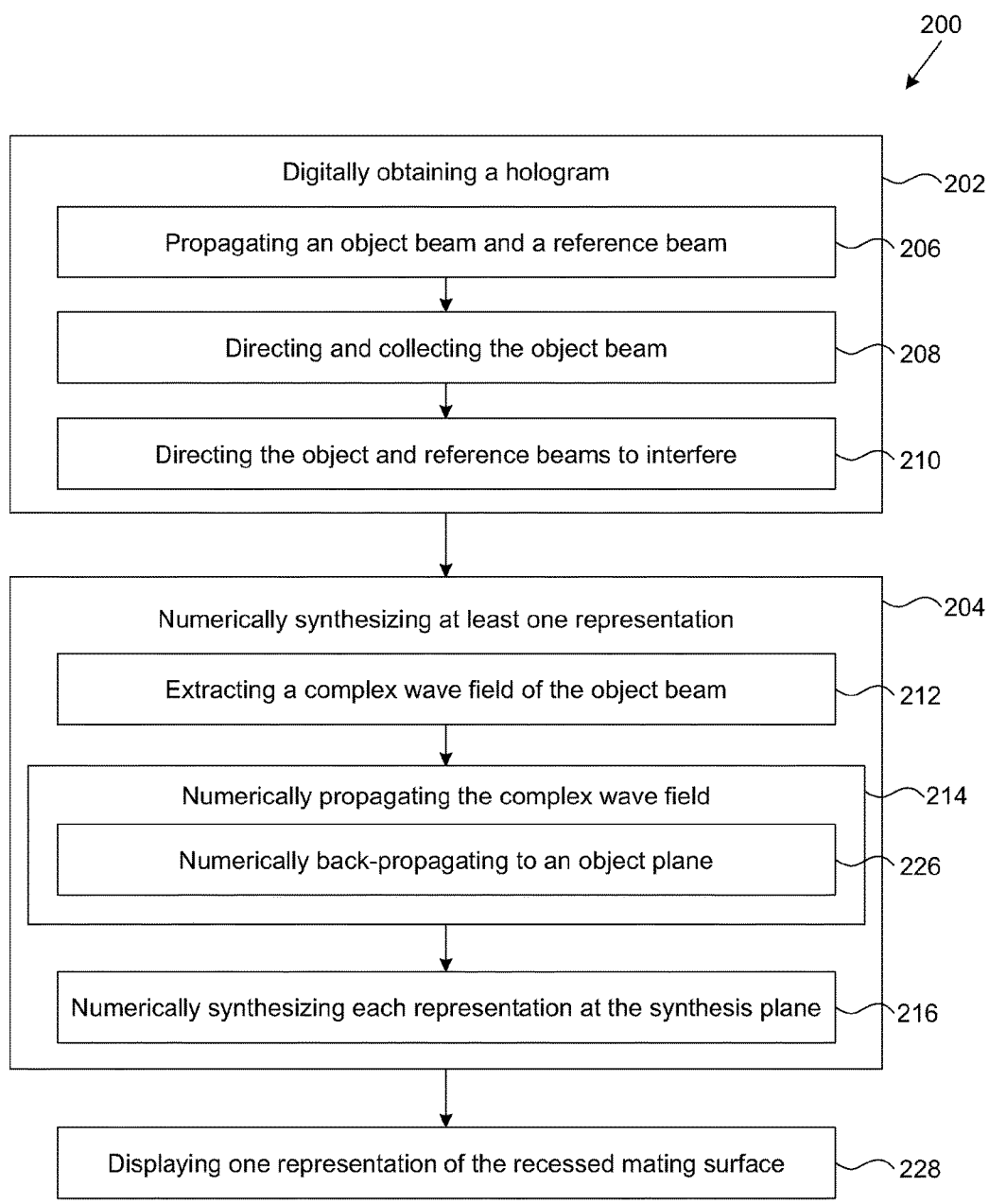

According to an aspect of the specification, there is provided a method 200 for inspecting a mating surface of an optical fiber connector. FIGS. 8A to 8C show flow charts of embodiments of the method 200, which could, by way of example, be performed with a portable inspection probe 20 such as those illustrated in FIGS. 2 to 6 or with an inspection system 150 such as those illustrated in FIGS. 7A and 7B.

Broadly described, the inspection method 200 synthesizes a representation of the mating surface of an optical fiber connector using a holographic approach. More specifically, and as will be further described hereinbelow, the inspection method 200 involves a step 202 of digitally obtaining a hologram of the mating surface under inspection followed by a step 204 of numerically processing the digitally obtained hologram in order to obtain at least one representation of the mating surface that allow assessing the condition thereof. In some embodiments, the inspection method 200 may include a step of numerical focusing that spares an operator from having to perform a mechanical focus adjustment while digitally obtaining the hologram of the mating surface. In these or other embodiments, the inspection method 200 may also include a step of compensating optical aberrations present in the optical components disposed in the path of the reference and object beams that are made to mutually interfere in the step of digitally obtaining the hologram.

Referring to FIGS. 8A to 8C, the inspection method 200 first includes a step 202 of digitally obtaining a hologram of the mating surface.

As will be understood by one of ordinary skill in the art, the step 202 of digitally obtaining a hologram may performed according to different acquisition and recording techniques. In the illustrated embodiment of FIGS. 8A to 8C, the step 202 of digitally obtaining a hologram first includes a substep 206 of propagating an object beam and a reference beam along respective object and reference optical paths. This substep 206 may include generating a coherent source beam and splitting the coherent source beam into the object beam and the reference beam. In addition, it may be an advantage of some embodiments that the propagation of the reference beam along the reference optical path is performed in a manner that minimize the number of specular reflections experienced by the reference beam, so as to preserve a high-quality reference beam.

The step 202 of digitally obtaining a hologram may also include a substep 208 of directing, along the object optical path, the object beam onto the mating surface and collecting the same upon reflection thereof by the mating surface using a probing optical assembly, wherein the probing optical assembly is not traversed by the reference beam.

The step 202 of digitally obtaining a hologram may further include a substep 210 of directing the object and reference beams to interfere at a holographic detection plane, thereby forming the hologram of the mating surface. This substep includes orienting the object and reference optical paths with respect to each other so that the reference beam and the object beam reflected from the mating surface and collected by the probing optical assembly meet at the holographic detection plane at a non-zero mutual angle, thereby enabling spatial heterodyne detection.

It will be understood that it may be an advantage of some embodiments that the substep 210 of directing the object and reference beams to interfere at a holographic detection plan need not involve mechanically positioning the image plane of the probing optical assembly on the holographic detection plane, since this may be performed during the step 204 of numerically processing the digitally obtained hologram, as described hereinbelow. Therefore, some embodiments eliminate the need for an operator to perform mechanical focus adjustments. However, as will also be discussed below, it is generally advantageous to position the holographic detection plane at the nominal position of the image plane, as given by the nominal position of the object. A deviation of the image plane from its nominal position will be corrected by numerical processing. For example, mechanical tolerance of common optical connectors allows for a deviation of the mating surface of 500 µm from its nominal position. Accordingly, if the magnification introduced by the lens is 5, a displacement of the object by 500 µm from its nominal position corresponds to the image plane being 2.5 mm away from the holographic detection plane, which will be corrected by numerical processing, to an accuracy of tens of micrometers or better.

Still referring to FIGS. 8A to 8C, the inspection method 200 then involves a step 204 of numerically synthesizing at least one representation of the mating surface of the optical fiber connector based on the hologram thereof. As for the step 202 of digitally obtaining a hologram, it will be understood that this step 204 may be performed using different known numerical methods.

For example, in the embodiment of FIGS. 8A to 8C, the step 204 of numerical synthesis may include a first substep 212 of extracting from the hologram of the mating surface a complex wave field of the object beam at a holographic detection plane. As used herein the term "complex wave field" or "complex wavefront" refers to a complex number, having both amplitude and phase information, characterizing the object beam subsequent to its reflection by the mating surface under inspection. As known in the art, holography generally provides a method by which the amplitude and phase of the object wave field can be recorded and extracted.

In order to extract the complex wave field from the digitally obtained hologram, one may consider Eq. (1) given above, which expresses the hologram as a two-dimensional intensity distribution $I(x, y)$ in the holographic detection plane xy0. It will be understood that in spatial heterodyne detection, extraction of the complex wave field of the object beam $U(x, y)$ may be achieved by first computing the Fourier transform of the recorded hologram $I(x, y)$, which exhibits the three angular frequency bands identified in Eq. (1), that is, a baseband defined by the zero-order terms, and two side bands, each representing respective interference terms.

As is also known in the art, spatial heterodyne detection allows the information regarding the phase and amplitude of the object beam $U(x,y)$ to be extracted by isolating either or both of the side-band terms. In a preferred embodiment of the inspection method 200, this can be achieved by first applying an appropriate digital bandpass filter to remove one of the side bands and the baseband (i.e. zero-order terms) followed by shifting the axes in the spatial-frequency (i.e.

Fourier) domain to remove the carrier (i.e. the reference) from the remaining side band. Alternatively, it would also be possible to retain and combine the two side-band terms, since they are complex conjugates of each other. In addition, the reference could also be removed by a division in the real-space domain, which would have the added benefit of taking into account possible spatial non-uniformity of power or phase.

Still referring to FIGS. 8A to 8C, the numerical synthesis step 204 may also include a substep 214 of numerically propagating the complex-wave field from the holographic detection plane to a synthesis plane, followed by a substep 216 of numerically synthesizing the at least one representation of the mating surface at the synthesis plane.

It will be understood by one of ordinary skill in the art that once the phase and amplitude of the complex wave field of the mating surface have been extracted from the spatially filtered Fourier-transformed hologram, at least one representation of the mating surface may be computed by numerically simulating the propagation of the object wave field to the synthesis plane. This numerical propagation may be performed by employing computational techniques and algorithms based on the Huygens-Fresnel-Kirchhoff diffraction integral formula and the Fresnel approximation thereof (see, e.g., O. K. Ersoy. *Diffraction, Fourier Optics and Imaging*. John Wiley and Sons, 2007). In particular, in the Fresnel approximation, a paraxial optics approximation applies and the Huygens-Fresnel-Kirchhoff diffraction integral reduces to a two-dimensional Fourier transform whose computation may be substantially faster. It will be understood, however, that embodiments of the inspection method are not limited to specific numerical propagation formalisms and that different formalisms may be employed in order to meet the performance, time or cost requirements of a particular application.

As mentioned briefly above, the inspection method according to some embodiments may also include numerical focusing and compensation of optical aberrations in the optical components disposed in the path of the reference and object beams.

Numerical focusing may be enabled by embodiments of the inspection method, since several image planes may be synthesized from a single digital hologram. Such computations may be carried out by changing the distance over which the complex-wave field of the object beam propagates from the digital holographic plane. It will be understood that numerical focusing may be advantageous in the context of the inspection of optical fiber components as it frees the operator from having to perform mechanical focus adjustments during the step 202 of digitally obtaining the hologram.

Referring to FIG. 8A, the substep 214 of numerically propagating the complex wave field of the object beam from the holographic detection plane to a synthesis plane may include numerical focusing embodied by a step 218 of numerically propagating the complex wave field from the holographic detection plane to at least one test image plane 218, followed by a step 220 of selecting one of the at least one test image plane as the synthesis plane.

For example, when the image plane of the object beam is located in the vicinity of the holographic detection plane, the complex wave field may be iteratively propagated and back-propagated to one or more test image planes located near the holographic detection plane in search of the image of mating surface of the optical fiber connector. Such iterations may be stopped when the periphery of the optical fiber enclosed in the optical connector is sharp and when the diameter of the optical fiber corresponds to the expected diameter $D_{expected}=M \times D_{real}$, where $D_{real}$ is the real diameter of the optical fiber and M is the magnification imposed on the object beam, both of which are known parameters. It will be understood that in this embodiment, because the numerical aperture on the image side is generally small enough, that is M times smaller than on the object side, the numerical propagation of the complex wave field may be performed in a paraxial approximation, which generally leads to a reduced computation time. Alternatively or additionally, the decision to stop the iterations can be based on an analysis of the spatial spectrum of the complex wave field at each test image plane. Specifically, because the light source used to generate the reference and object beams generally has high coherence, a high-frequency ripple will generally be observed in the image when proper focus is not achieved. In order to numerically determine the optimal position of the synthesis plane, the ripple in the image should be minimized, which can be achieved by minimizing the high-frequency components of the complex wave field spatial spectrum.

In the course of such computational beam propagation, embodiments of the inspection method may also compensate, at least partially, optical aberrations, which may be present along the object and reference optical paths. If not corrected, these optical aberrations may degrade the object and reference beams, as well as the at least one representation numerically synthesized from the digital hologram, thereby potentially undermining the validity of the inspection method. Of course, it will be understood that in other embodiments, these aberrations may be satisfactorily mitigated by the choice of high-tolerance optical components and alignment. Although this could likely introduce a substantial additional cost to a commercial inspection probe, this may nonetheless be acceptable in some situations. In this case, the numerical correction or compensation for optical aberrations may not be necessary. Accordingly, some embodiments of the inspection method allow at least partial numerical correction or compensation for optical aberrations in optical components disposed in the object and reference beam paths during acquisition of the digital hologram corresponding to the mating surface.

As known in the art, optical aberrations may include, without being limited to, chromatic and spherical aberrations, astigmatism, image distortion and defocusing. Furthermore, it is also known in the art that different optical components may be predominantly susceptible to different types of optical aberrations, and hence the nature of the numerical compensation applied to these respective components will be targeted accordingly. Real lenses generally do not significantly affect the amplitude of optical beams propagating therethrough, but may introduce additional phase terms compared to ideal lenses, in particular those responsible for spherical aberrations.

As one of ordinary skill in the art will understand, this compensation may be achieved by mathematically modeling optical components such as lenses, beam splitters and apertures in terms of their respective optical transfer functions, which incorporate the effects of optical aberrations affecting the real imperfect optical components. Hence, when the complex-wave field of the object beam extracted from the digitally recorded hologram is numerically propagated from the holographic detection plane to the synthesis plane in order to synthesize the at least one representation of the mating surface, optical aberrations present in the actual optical components may, at least to some extent, be taken into account and corrected for. It will be understood that this may advantageously enhance the accuracy and reliability of the inspection method according to some embodiments, and/or reduce the cost and complexity of manufacturing the inspection device.

Optionally, in some embodiments, supplemental measurements may be performed to calibrate optical aberrations and subsequently compensate for them numerically, at least partially, based on this calibration procedure.

It will be understood that by eliminating the need to perform mechanical focus adjustments and by compensating for optical aberrations, some embodiments of the inspection method may advantageously allow inspection of a multi-fiber connector from a single holographic acquisition. Indeed, inspecting a multi-fiber connector in a single acquisition generally requires a larger field of view than that for inspecting a single-fiber connector. However, a larger field of view generally increases the susceptibility to optical aberrations. Therefore, by relying on numerical focusing and numerical compensation of optical aberrations, some embodiments of the inspection method make it possible to use larger field of views, thus enabling inspection of multi-fiber connectors using a single holographic acquisition. In contrast, conventional multi-fiber inspection methods generally involve time-consuming manual adjustment by the user since a separate image usually must be acquired for each fiber or a small subset of fibers in the multi-fiber connector.

Referring to FIG. 8B, the substep 214 of numerically propagating the complex wave field of the object beam from the holographic detection plane to a synthesis plane may include a step 222 of numerically back-propagating the complex wave field from the holographic detection plane to an intermediate surface by numerical back-propagating the complex wave field through a first virtual probing optical assembly.

The numerical propagation of the complex wave field through this first virtual probing assembly may be performed in the paraxial approximation and by employing an optical transfer function that accounts for the optical aberrations affecting the optical probing assembly actually used to direct the object beam onto the mating surface and for collecting the same upon specular reflection thereof by the mating surface. It will be understood that the optical aberrations that may have affected the complex wave field extracted at the digital holographic plane are compensated at least to some extent when the complex wave field reaches the intermediate surface.

Still referring to FIG. 8B, the substep 214 of numerically propagating the complex wave field of the object beam from the holographic detection plane to a synthesis plane may also include a step 224 of numerically propagating the complex wave field from the intermediate surface to an image plane corresponding to the synthesis plane by numerically propagating the complex wave field through a second virtual probing optical assembly that is free of optical aberrations. For example, the second virtual probing optical assembly may be embodied by a perfect virtual lenses or a virtual parabolic mirror. Numerical focusing may then be applied by employing techniques described hereinabove with reference to FIG. 8A. Using such techniques, the image plane corresponding to the synthesis plane may then be found. It will be understood that because the numerical aperture of the object beam is generally small everywhere between the holographic detection plane and the intermediate surface, the numerical propagation of the complex wave field can be performed in a paraxial approximation, which generally reduce computation time. In contrast, it is to be noted that the paraxial approximation generally does not hold on the optical path between the probing optical assembly and the object.

Referring to FIG. 8C, the substep 214 of numerically propagating the complex wave field of the object beam from the holographic detection plane to a synthesis plane may alternatively include a step 226 of numerically back-propagating the complex wave field from the holographic detection plane to an object plane corresponding to the synthesis plane. The object plane is positioned at the mating surface of the optical fiber connector and back-propagation is performed by employing an optical transfer function of the probing optical assembly that accounts for optical aberrations thereof. Numerical focusing may then also be applied by employing techniques described hereinabove with reference to FIG. 8A. It is however noted that, in some embodiments, the numerical aperture between the probing optical assembly and the mating surface may become too large such that the paraxial approximation is no longer sufficiently valid and hence more sophisticated models such as the Huygens-Fresnel-Kirchhoff framework may need to be employed, thereby potentially increasing the required computation time and resources.

Referring back to FIGS. 8A to 8C, once the at least one representation of the mating surface has been numerically synthesized at the synthesis plane, the inspection method may further include a step 228 displaying one of the at least one representation of the mating surface for inspection thereof by a user. As will be understood by one of ordinary skill in the art, the at least one representation that is displayed may be based on one or a combination of amplitude and phase images of the mating surface of the optical fiber connector. For example, in one embodiment, a digital image of the mating surface may be provided on which identified defects and foreign particles are emphasized by appropriate color indicators.

Additionally or alternatively, the numerically synthesized at least one representation of the mating surface may be compared against at least one quality criterion, which may be pre-programmed or user-defined, in order to provide an indication of the number and severity of defects and foreign bodies on the mating surface under inspection. The result of the comparison analysis may be displayed as simple pass/fail or pass/dirty/defects indicators using differently colored LED indicators.

Of course, numerous modifications could be made to the embodiments above without departing from the scope of the invention.

The invention claimed is:

1. A portable inspection probe for the inspection of a recessed mating surface of an optical fiber connector to be used with a rigid probe tip connectable thereto and shaped to provide optical access to the recessed mating surface, the portable inspection probe comprising:
    a handheld portable housing comprising a tip connector to which the rigid probe tip is connectable, the rigid probe tip protruding from the handheld portable housing upon connection to the tip connector; and
    a digital holographic detection module accommodated at least partly inside the handheld portable housing and configured to propagate an object beam and a reference beam along respective object and reference optical paths and to direct, without mechanical focus adjustment or control, the object and reference beams to interfere at a holographic detection plane after reflection of the object beam from the recessed mating surface, thereby forming the hologram of the recessed mating surface, the digital holographic detection module comprising:
- a light source assembly configured to generate the object and reference beams;
- a detector array positioned at the holographic detection plane and configured to digitally record the hologram of the recessed mating surface; and
- a probing lens assembly configured to direct the object beam onto the recessed mating surface and to collect the object beam after reflection from the recessed mating surface.

2. The portable inspection probe according to claim 1, wherein the probing lens assembly is not traversed by the reference.

3. The portable inspection probe according to claim 1, wherein the object and reference beams meet at the holographic detection plane at a non-zero mutual angle.

4. The portable inspection probe according to claim 1, wherein the light source assembly comprises a coherent light source configured to generate a coherent source beam and a beam splitter configured to split the coherent source beam into the object beam and the reference beam.

5. The portable inspection probe according to claim 4, wherein the coherent light source is a laser source.

6. The portable inspection probe according to claim 1, wherein the probing lens assembly comprises a triplet lens.

7. The portable inspection probe according to claim 1, wherein the digital holographic detection module further comprises a beam combiner positioned in the object and reference optical paths, so as to combine and direct the reference and object beams to interfere at the holographic detection plane.

8. The portable inspection probe according to claim 7, wherein the digital holographic detection module further comprises collimation optics configured to collimate the reference beam before interference with the object beam.

9. The portable inspection probe according to claim 8, wherein the collimation optics comprises a triplet lens.

10. The portable inspection probe according to claim 1, further comprising a processor configured to numerically synthesize at least one representation of the recessed mating surface of the optical fiber connector based on the hologram thereof.

11. The portable inspection probe according to claim 10, wherein the processor is further configured to characterize at least one quality criterion from the numerically-synthesized at least one representation of the recessed mating surface.

12. The portable inspection probe according to claim 10, wherein the processor is further configured to:
- extract from the hologram of the recessed mating surface a complex wave field of the object beam at a holographic detection plane;
- numerically propagate the complex wave field from the holographic detection plane to a synthesis plane; and
- numerically synthesize the at least one representation of the recessed mating surface at the synthesis plane.

13. The portable inspection probe according to claim 12, wherein the processor is further configured to numerically focus the complex wave field of the object beam at the synthesis plane by numerically propagating the complex wave field from the holographic detection plane to at least one test image plane, and selecting one of the at least one test image plane as the synthesis plane.

14. An inspection system comprising:
- the portable inspection probe according to claim 1; and
- a processor configured to:
  - receive the hologram of the recessed mating surface of the optical fiber connector digitally recorded by the digital holographic detection module of the portable inspection probe; and
  - numerically synthesize at least one representation of the recessed mating surface based on the hologram thereof.

15. The inspection system according to claim 14, wherein the processor is further configured to characterize at least one quality criterion from the numerically-synthesized at least one representation of the recessed mating surface.

16. The inspection system according to claim 14, wherein the processor is further configured to:
- extract from the hologram of the recessed mating surface a complex wave field of the object beam at a holographic detection plane;
- numerically propagate the complex wave field from the holographic detection plane to a synthesis plane; and
- numerically synthesize the at least one representation of the recessed mating surface at the synthesis plane.

17. The inspection system according to claim 16, wherein the processor is further configured to numerically focus the complex wave field of the object beam at the synthesis plane by numerically propagating the complex wave field from the holographic detection plane to at least one test image plane, and selecting one of the at least one test image plane as the synthesis plane.

18. The portable inspection probe according to claim 1, further comprising said rigid probe tip configured to be optically coupled to the digital holographic detection module and shaped to provide optical access to the recessed mating surface.

19. A method for inspecting a recessed mating surface of an optical fiber connector with a portable inspection probe having a rigid probe tip connected thereto and shaped to provide optical access to the recessed mating surface, the recessed mating surface of the optical fiber connector being located in a recess, the method comprising the steps of:
- a) inserting the rigid probe tip into the recess to provide optical access to the recessed mating surface while holding the handheld portable housing;
- b) digitally obtaining a hologram of the recessed mating surface, comprising:
  - i) propagating an object beam and a reference beam along respective object and reference optical paths;
  - ii) along the object optical path, directing the object beam onto the recessed mating surface and collecting the same upon reflection thereof by the recessed mating surface using a probing optical assembly, wherein the probing optical assembly is not traversed by the reference beam;
  - iii) directing, without mechanical focus adjustment or control, the object and reference beams to interfere at a holographic detection plane, thereby forming the hologram of the recessed mating surface; and
- c) numerically synthesizing at least one representation of the recessed mating surface of the optical fiber connector based on the hologram thereof.

20. The method according to claim 19, wherein step c) comprises the substeps of:
- i) extracting from the hologram of the recessed mating surface a complex wave field of the object beam at a holographic detection plane;
- ii) numerically propagating the complex wave field from the holographic detection plane to a synthesis plane; and iii) numerically synthesizing the at least one representation of the recessed mating surface at the synthesis plane.

21. The method according to claim 20, wherein substep ii) of step c) comprises numerically focusing the complex wave field of the object beam at the synthesis plane, said numerically focusing comprising:
   numerically propagating the complex wave field from the holographic detection plane to at least one test image plane; and
   selecting one of the at least one test image plane as the synthesis plane.

22. The method according to claim 20, wherein substep ii) of step c) comprises:
   numerically back-propagating the complex wave field from the holographic detection plane to an intermediate surface by numerical back-propagating the complex wave field through the probing optical assembly by employing an optical transfer function that accounts for optical aberrations thereof, thereby compensating for said optical aberrations; and
   numerically propagating the complex wave field from the intermediate surface to an image plane corresponding to the synthesis plane by numerically propagating the complex wave field through a virtual optical probing assembly that is free of optical aberrations.

23. The method according to claim 22, wherein the numerically back-propagating and the numerically propagating employ a paraxial approximation.

* * * * *